US006985616B2

(12) United States Patent
Ganz et al.

(10) Patent No.: US 6,985,616 B2
(45) Date of Patent: Jan. 10, 2006

(54) AUTOMATED VERIFICATION AND INSPECTION DEVICE FOR SEQUENTIALLY INSPECTING MICROSCOPIC CRYSTALS

(75) Inventors: Brian L. Ganz, Carlsbad, CA (US); David W. Jewell, San Diego, CA (US); Mandel W. Mickley, Oceanside, CA (US); John Andrew Moulds, Encinitas, CA (US); Christopher T. Brovold, Carlsbad, CA (US); John A. Adams, Escondido, CA (US)

(73) Assignee: RoboDesign International, Inc., Carlsbad, CA (US)

( * ) Notice: Subject to any disclaimer, the term of this patent is extended or adjusted under 35 U.S.C. 154(b) by 0 days.

(21) Appl. No.: 09/982,048

(22) Filed: Oct. 18, 2001

(65) Prior Publication Data

US 2003/0099382 A1 May 29, 2003

(51) Int. Cl.
*G06K 9/00* (2006.01)
*G06K 9/62* (2006.01)

(52) U.S. Cl. ..................................... 382/133; 382/224
(58) Field of Classification Search ................ 382/133, 382/108, 147, 148, 128, 224; 117/201, 68; 356/30; 438/16
See application file for complete search history.

(56) References Cited

U.S. PATENT DOCUMENTS

| | | | |
|---|---|---|---|
| 4,000,417 A | 12/1976 | Adkisson | 250/201 |
| 4,741,043 A | 4/1988 | Bacus | 382/6 |
| 5,473,706 A | 12/1995 | Bacus | 382/133 |
| 5,544,254 A * | 8/1996 | Hartley et al. | 382/108 |
| 5,689,317 A * | 11/1997 | Miller | 349/80 |
| 5,714,970 A * | 2/1998 | Bos et al. | 345/88 |
| 5,741,648 A | 4/1998 | Hemstreet | 435/6 |
| 6,002,476 A * | 12/1999 | Treado | 356/301 |
| 6,061,086 A * | 5/2000 | Reimer et al. | 382/141 |
| 6,226,392 B1 | 5/2001 | Bacus | 382/128 |
| 6,246,785 B1 | 6/2001 | Molnar | 382/133 |
| 6,259,960 B1 | 7/2001 | Inokuchi | 700/110 |
| 6,262,838 B1 | 7/2001 | Montagu | 359/392 |
| 6,265,232 B1 | 7/2001 | Simmons | 438/14 |
| 6,368,402 B2 * | 4/2002 | DeTitta et al. | 117/68 |
| 6,388,788 B1 * | 5/2002 | Harris et al. | 250/234 |
| 2003/0194377 A1 * | 10/2003 | Carroll et al. | 424/45 |

FOREIGN PATENT DOCUMENTS

GB 2310925 A * 9/1997

OTHER PUBLICATIONS

Automation Update, www.texonics.com/Newsletters/Archived Articles/1998/0198newsletter.pdf.*
Jurisica, I., et al., "Intelligent Decision Support for Protein Crystal Growth" *IBM Systems Journal*, vol. 40, No. 2, 2001, pp. 394-408.

* cited by examiner

*Primary Examiner*—Vikkram Bali
(74) *Attorney, Agent, or Firm*—John R. Ross, III; John R. Ross

(57) ABSTRACT

A method and device for inspecting and classifying a plurality of microscopic crystals. An indexing device sequentially places microscopic crystals in camera-view of a camera. The camera takes images of the microscopic crystals and then transfers the images to a computer where the are received. The computer then classifies the images. The computer is also programmed to control the indexing device and the camera. In a preferred embodiment, the microscopic crystals are protein crystals that have been grown in the wells of micro-well plates. Also, preferably, the computer is programmed to automatically classify the images.

41 Claims, 26 Drawing Sheets

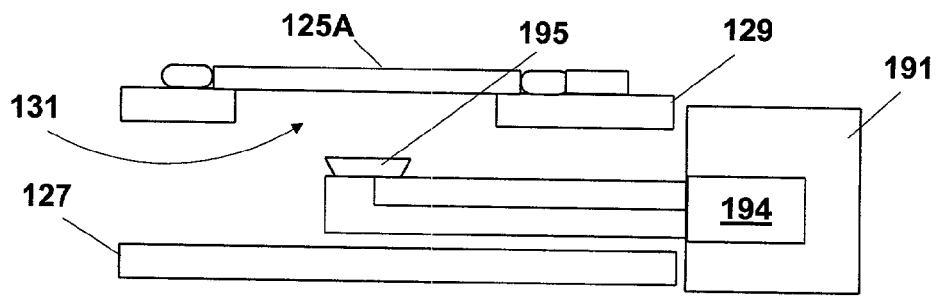
FIG. 14
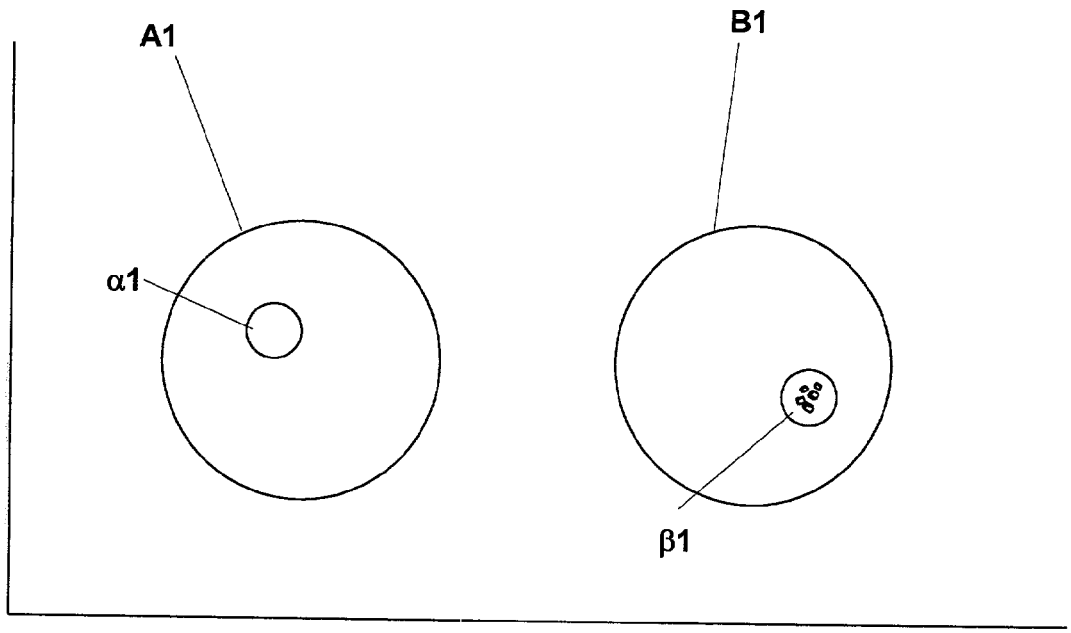
FIG. 15
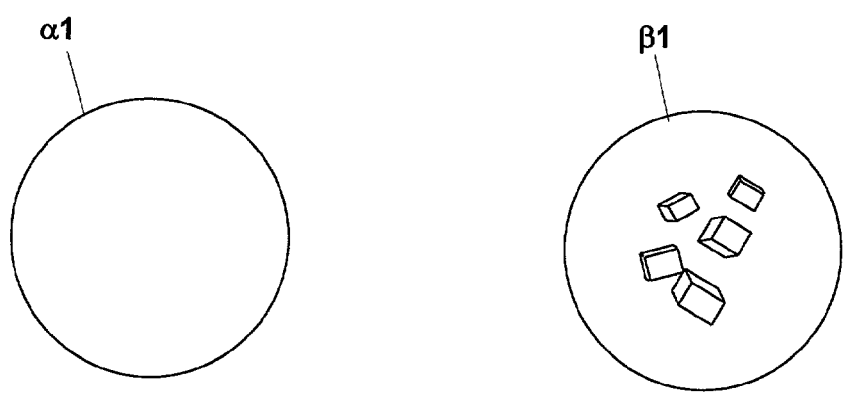
FIG. 16
FIG. 17

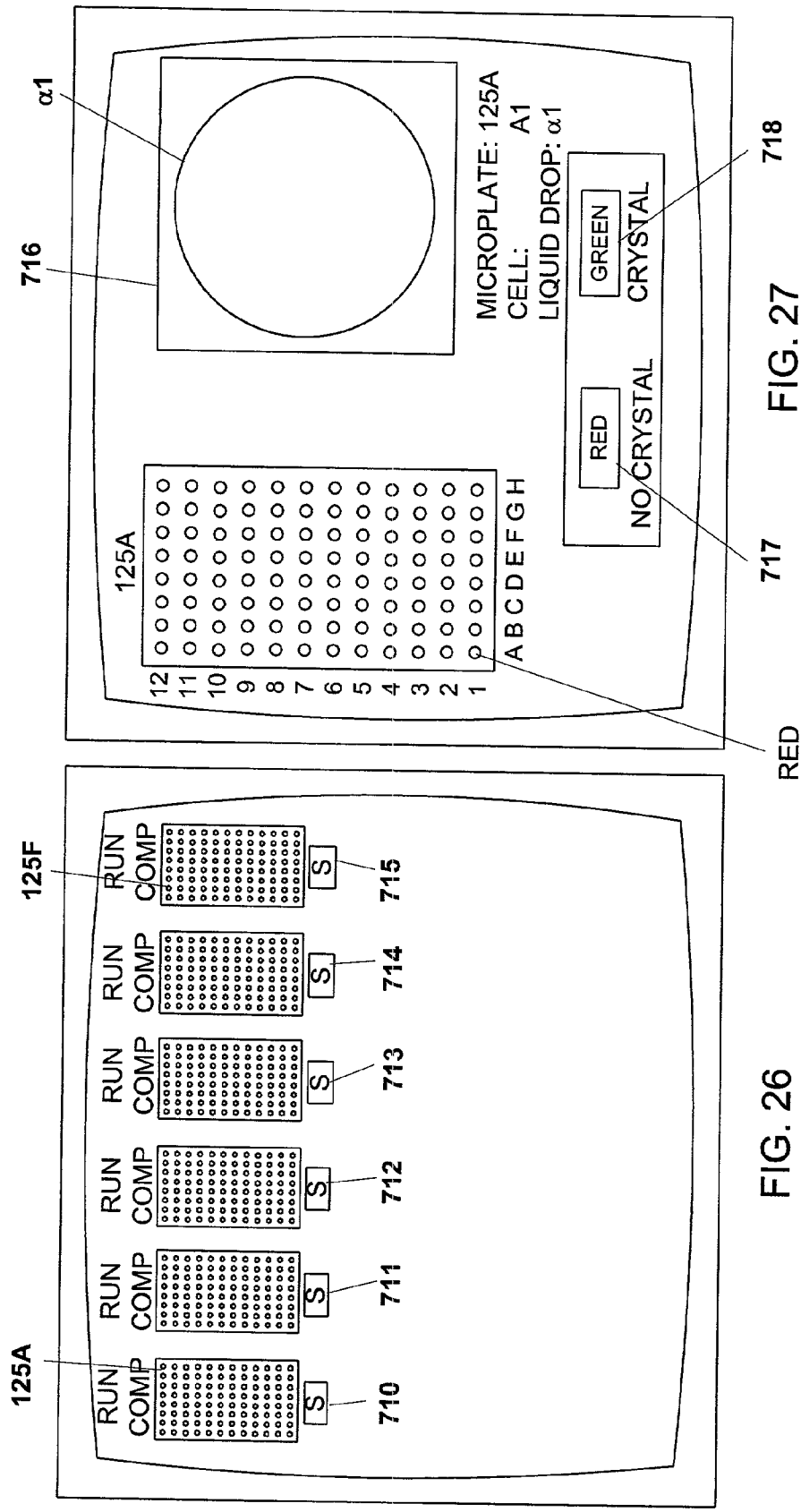

AUTOMATED VERIFICATION AND INSPECTION DEVICE FOR SEQUENTIALLY INSPECTING MICROSCOPIC CRYSTALS

BACKGROUND OF THE INVENTION

The determination of the three dimensional atomic structure of matter is one of the most important areas of pure and applied research. One way in which the three dimensional atomic structure of matter can be determined is through X-ray crystallography. X-ray crystallography utilizes the diffraction of X-rays from crystals in order to determine the precise arrangement of atoms within the crystal. The result may reveal the atomic structure of substances such as metal alloys, deoxyribonucleic acid (DNA), or the structure of proteins.

There are very important benefits to knowing the accurate molecular structure of a protein crystal. For example, once the molecular structure is known, a drug designer can more effectively develop effective therapeutic agents and drugs. However, despite its promises, X-ray crystallography is limited by the fact that it is very difficult to grow successful crystals.

Prior Art Method of Growing Crystals

Protein crystals are commonly grown in the wells of micro-well plates. A micro-well plate is also known as a micro-titer plate or a microplate. Micro-well plates typically come with either 24, 48, 96, 384 or 1536 wells. A 96-well micro-well plate is shown in detail in FIG. 2. There are a variety of methods in which protein crystals may be grown. Five common ways are summarized below.

Hanging Drop Method

One of the main techniques available for growing crystals, known as the hanging-drop or vapor diffusion method, is a method wherein a drop of a solution containing protein is applied to a glass cover slip and placed upside down in an apparatus such as a vapor diffusion chamber where conditions lead to supersaturation in the protein drop and the initiation of precipitation of the protein crystal.

Sitting Drop Method

Another method is the sitting drop method where the drop sits in a small well adjacent the growing solution instead of hanging over it. This method provides a more stable drop and location.

Aqueous Drop in Oil Method

Another method is the aqueous drop in oil method. The drop is placed in a micro-well and is covered with an oil based solution. The drop stays at the bottom of the well as the crystal grows.

Dialysis Method

In another method referred to as the dialysis method (also called microbatch crystallization), the protein solution is contained within a semi-permeable size exclusion membrane and then placed in a solution of fixed pH and precipitant concentration. As the precipitant diffuses through the membrane into the protein compartment, the solubility of the protein is reduced and crystals may form.

Gel Crystal Growth Method

This method involves the placement of a gel into the end of small diameter glass capillaries. After the solutions have gelled, a protein solution is placed into one end (top) of the capillary and the other end is submerged in a solution of precipitating agent. If the conditions are appropriately selected, crystal growth occurs at a point in the gel where the protein and precipitating agent reach the proper concentrations as the solutions slowly mix by diffusion. Since this is a diffusion limited process, it thus only occurs after an extended period of time. Crystals however, grown by this method are often larger and of higher quality.

Regardless of the method chosen, protein crystal growth is a very delicate and time-consuming process. It can take several days to several months before crystal of sufficient size and quality are grown and ready for x-ray crystallography. The current minimum size that is typically stated is a crystal of at least 50 microns thick by 100 microns in extent. The protein crystal growing environmental conditions need to be rigorously maintained, from the chemistry, to the surrounding air humidity and temperature, cleanliness to prevent contamination, and even lighting conditions. A protein crystallographer working with unknown protein families may only be about 5% successful in growing proper sized quality crystals. With this success rate, for example, a 96-well micro-well plate may only have 5 wells in which good crystals are growing.

Prior Art Inspection of Crystal Growth

Currently, a laboratory technician, or operator, aided by a microscope and a laboratory notebook manually inspects crystals grown in micro-well plates. To inspect a micro-well plate, a laboratory technician dons a clean-room gown suit and enters a cold room in which the crystals are growing. The technician then puts a micro-well plate underneath the microscope and examines each well in the micro-well plate until all of the wells in the micro-well plate have been inspected. The technician then makes a mental judgement as to how he shall classify (also known as "score") the crystal. For example, the technician may feel that he is observing an image that shows "grainy precipitation" or "ugly precipitation". Or, he may feel that the image shows "no crystal growth". The technician then records the classification into a laboratory notebook.

The above system is riddled with opportunities for human error. An operator, manually inspecting a 96-well micro-well plate will take approximately 5 to 20 minutes depending on the skill of the operator and the number of wells that contain interesting features, microcrystals, or crystals. The operator may be subject to physical fatigue, suffer eyestrain, and may be uncomfortably cold in the temperature controlled and generally high humidity room. The operator can be tired and confused and can easily make errors in manually recording data in the notebook. For example, the operator may observe crystal growth at well H5 (FIG. 2), but incorrectly record in the notebook that the crystal growth was at well H6. Additional transcription errors may occur when the data is transferred to a computer database.

Research efforts are underway to try to solve the above problem, but they are inadequate for the needs of the industry. One such effort is described in Jurisica et al. "Intelligent Decision Support for Protein Crystal Growth" *IBM systems Journal*, Vol. 40, No 2, 2001. Another such effort is described at the Website www.dsitech.com.

What is needed is a better device and method for inspecting crystal growth.

SUMMARY OF THE INVENTION

The present invention provides a method and device for inspecting and classifying a plurality of microscopic crystals. An indexing device sequentially places microscopic crystals in camera-view of a camera. The camera takes images of the microscopic crystals and then transfers the images to a computer where the are received. The computer then classifies the images. The computer is also programmed to control the indexing device and the camera. In a preferred embodiment, the microscopic crystals are protein crystals that have been grown in the wells of micro-well plates. Also, preferably, the computer is programmed to automatically classify the images.

BRIEF DESCRIPTION OF THE DRAWINGS

FIG. 14 shows a side view of the light source shining upwards onto a micro-well plate.

FIG. 15 shows a magnified view of two wells of a micro-well plate, wherein each well has a drop of liquid.

FIGS. 16 and 17 show a detail view of the drops of liquid shown in FIG. 15.

FIG. 26 shows a preferred monitor screen after a run has been completed.

FIGS. 27 and 28 show details of other preferred monitor screens.

DETAILED DESCRIPTION OF A PREFERRED EMBODIMENT

A detailed description of a preferred embodiment of the present invention can be described by reference to the drawings.

Figure 1:
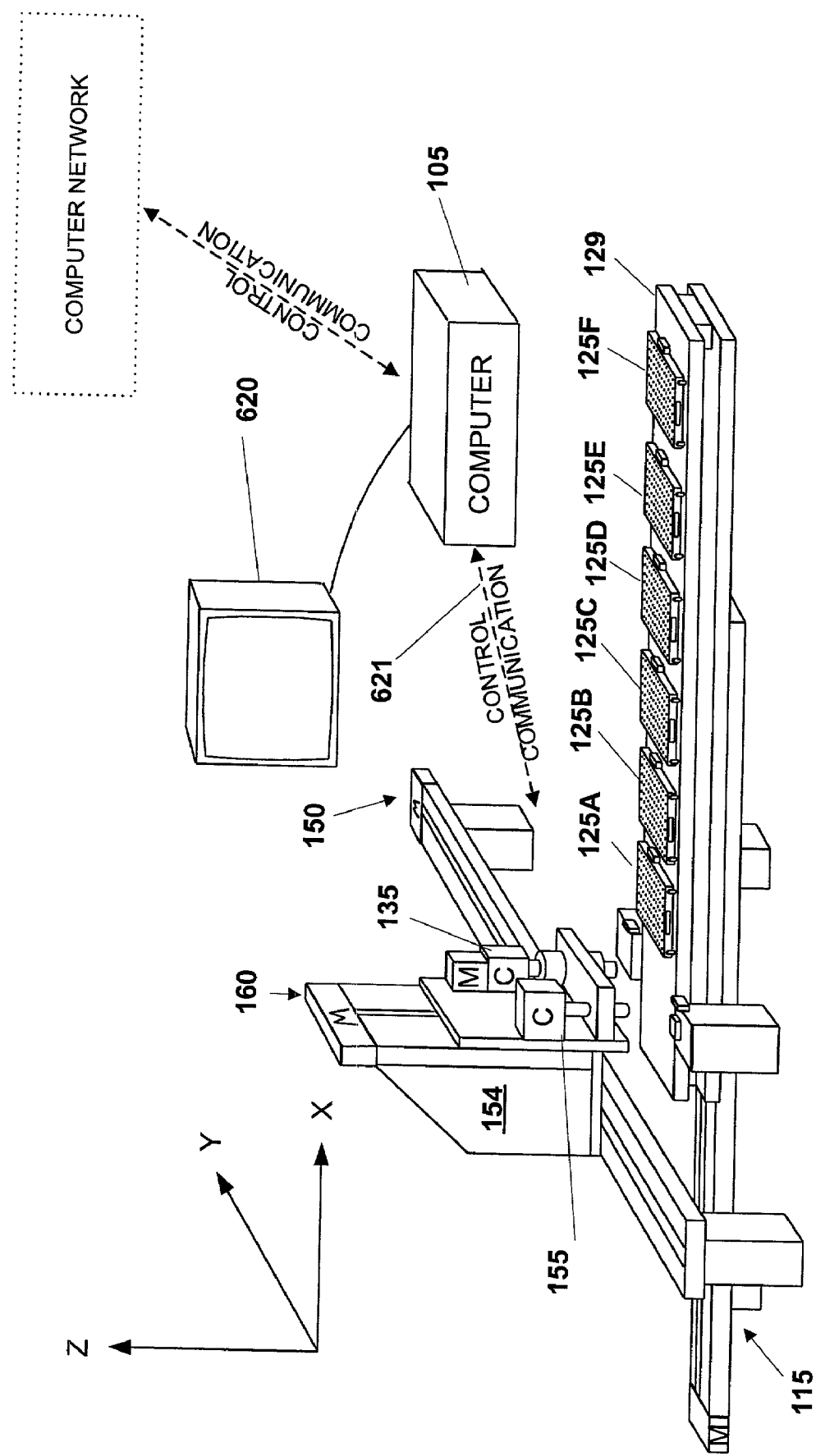
FIG. 1 shows a preferred embodiment of the present invention.

FIG. 1 shows a preferred embodiment of the present invention. Micro-well plates 125A–125F are placed on fixture plate 129. In a preferred embodiment, each micro-well plate has 96 wells. Each well has a drop of liquid in which microscopic protein crystals may be growing. Computer 105 automatically controls linear actuators 115, 150 and 160. Linear actuator 115 moves fixture plate 129 along the x-axis. Linear actuator 150 moves moving base 154 along the y-axis, and linear actuator 160 moves moving plate 162 along the z-axis. n The computer coordinates the movement of the linear actuators to properly position cameras 155 and 135 above each well of each micro-well plate 125A–125F in sequence. Preferably, cameras 155 and 135 are high-resolution ⅔ inch CCD cameras, with 1,300 horizontal pixel elements by 1,030 vertical elements. Each element is preferably 6.7 microns square with a sensing area of 8.7 mm by 6.9 mm. Cameras 155 and 135 take images of each well and transmit the images to computer 105 where they are digitized into a image data array of approximately 1,296 horizontal pixels by 1,000 vertical pixels by 8 bits of gray level representing the intensity (0 to 255) of each pixel. These digitized images are automatically recorded in the database of computer 105 and can be analyzed and scored by an operator via monitor 620. The digitized images may be further processed, analyzed, and the contents of the individual well scored by computer 105 executing program instructions to perform calculations on the image data array. In a preferred embodiment, computer 105 is connected via a communication/control line to a computer network. In this manner, the present invention can be controlled from a remote computer. Likewise, images and data can be transmitted to the remote computer.

Figure 2:
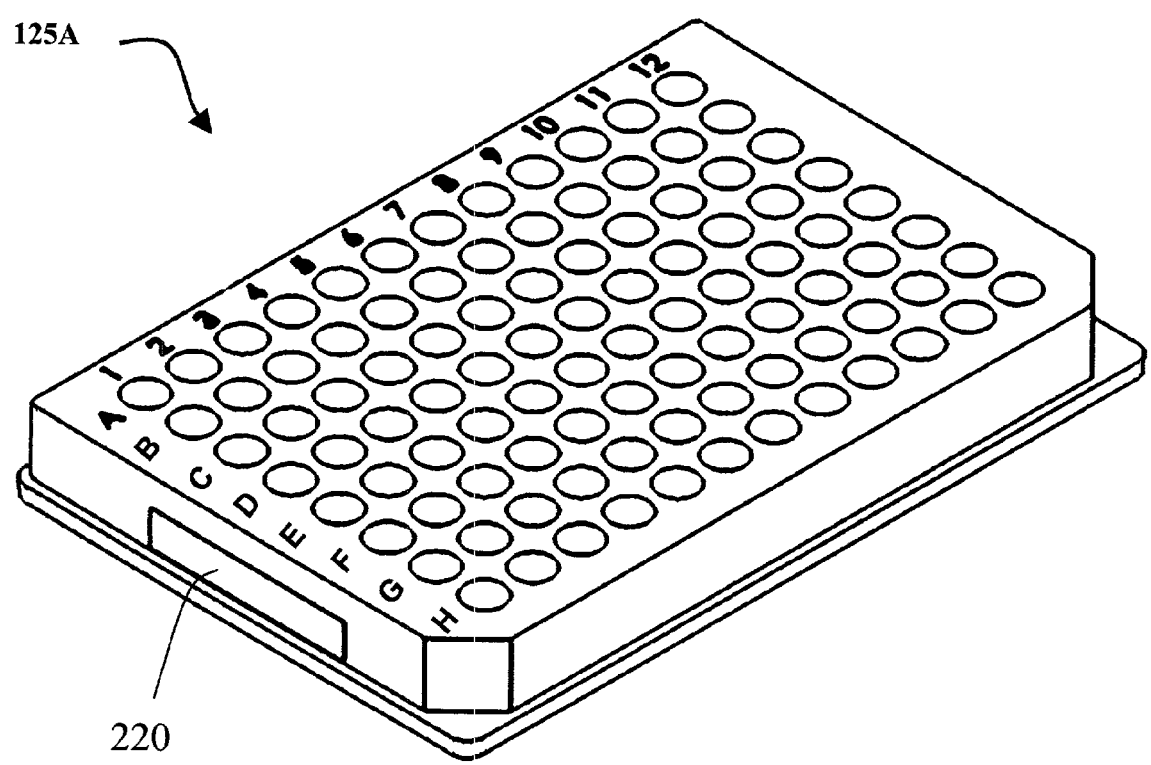
FIG. 2 shows a micro-well plate.

Sequence of Operation of a Preferred Embodiment Micro-Well Plates Loaded onto the System As shown in FIG. 1, six 96-well micro-well plates 125A–125F have been placed (either by an operator or by an external loading robot) onto fixture plate 129. A 96 well micro-well plate 125A is shown in FIG. 2. Micro-well plate 125A has wells labled A1 through H12 and a bar code label 220. Micro-well plate 125A is available from Nalge-Nunc International, with U.S. offices in Rochester, N.Y. Fixture plate 129 will hold 24, 48, 96, 384, or 1536 well micro-well plates since the micro-well plate external width and length are fairly standard in the industry. The 96 well micro-well plate will be used to illustrate the present invention.

Figure 3:
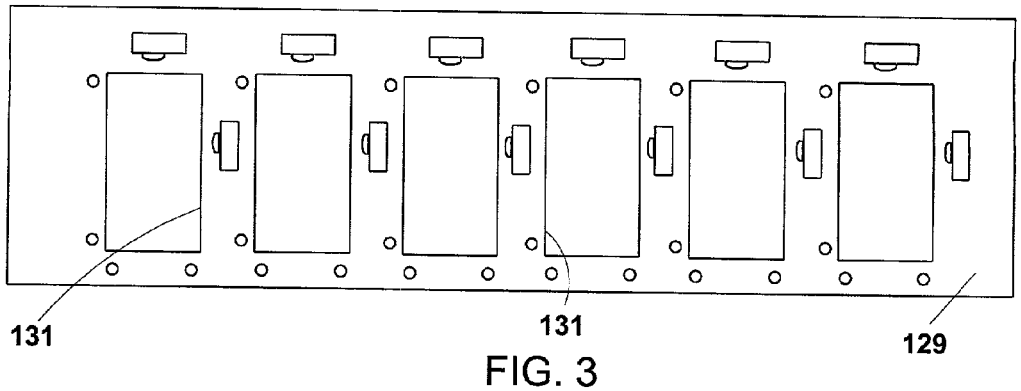
FIG. 3 shows a top view of the fixture plate.

FIG. 3 shows a top view of fixture plate 129 just prior to loading micro-well plates 125A–125F. Fixture plate 129 has six cutout sections 131 that are just slightly smaller in length and width than micro-well plates 125A–125F.

Figure 4:
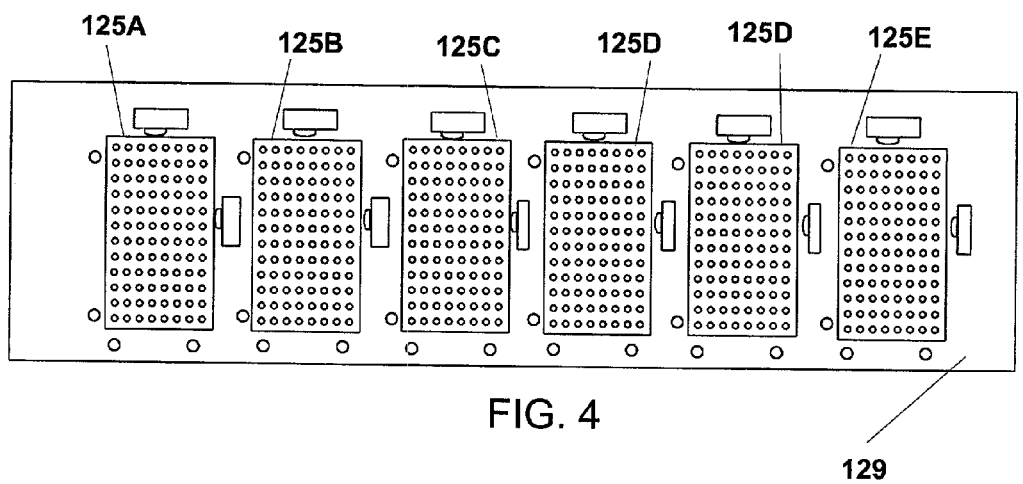
FIGS. 4 and 5 show top views of micro-well plates on the fixture plate.

FIG. 4 shows a top view of micro-well plates 125A–125F immediately after they have been placed on fixture plate 129.

Figure 5:
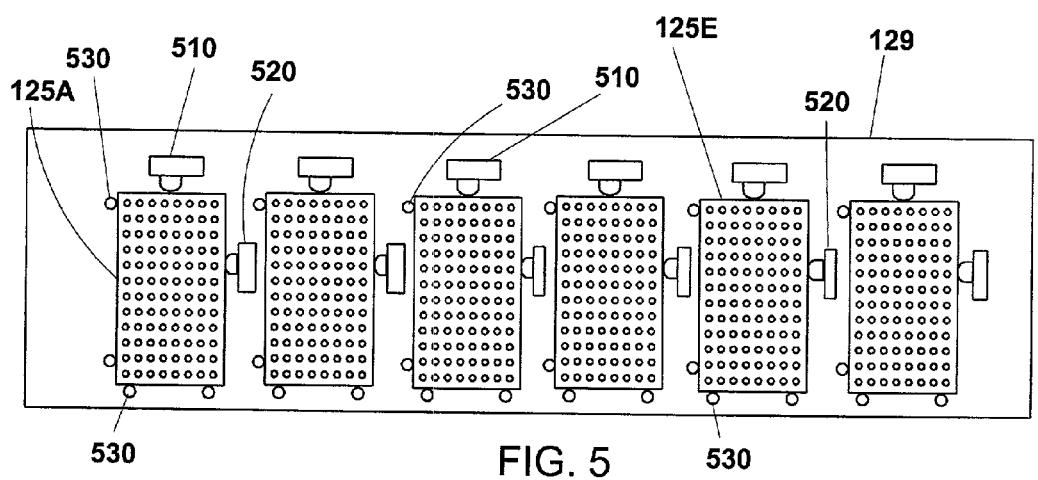

After the operator has placed micro-well plates 125A–125F onto fixture plate 129 as shown in FIG. 4, he enters the command into computer 105 (FIG. 1 and FIG. 6) to expand detents 510 and 520 (FIG. 5). The expansion of detents 510 and 520 firmly secures micro-well plates 125A–125F against plate stops 530.

Recording the Bar Code Information for the Micro-Well Plates

Figure 7:
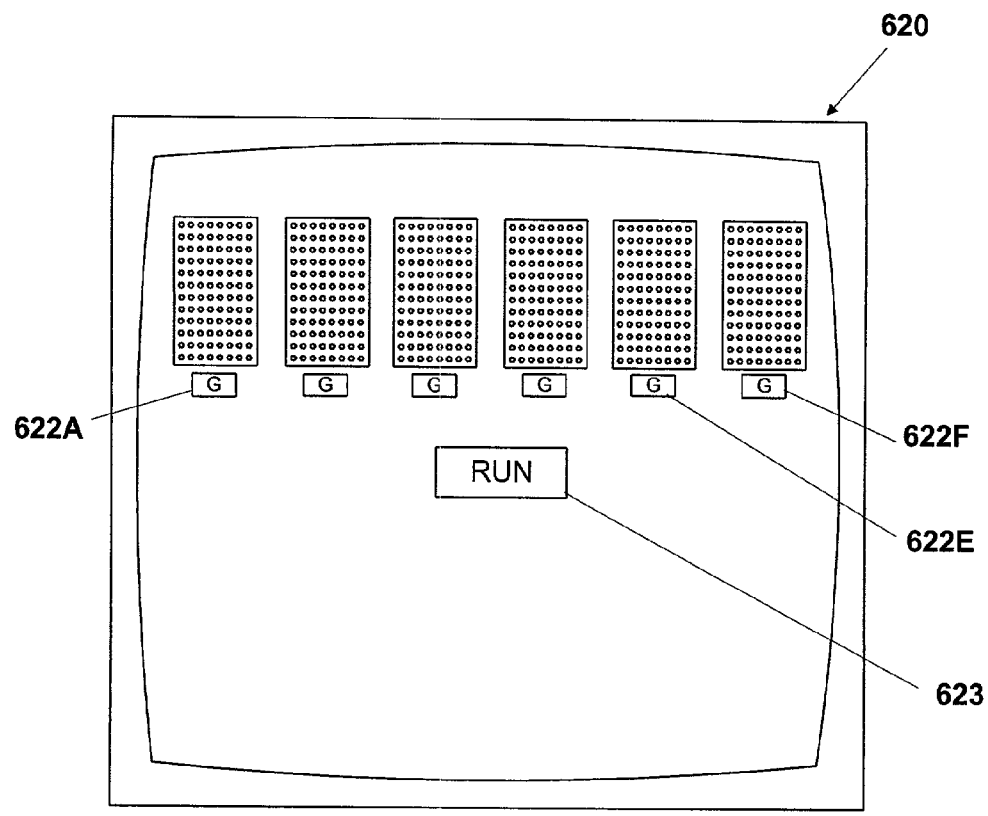
FIG. 7 shows a preferred monitor.

Computer 105 (FIG. 1) has been programmed to accept inputs from an operator. FIG. 7 shows a display representing micro-well plates 125A–125F on the screen of monitor 620. In FIG. 7, the operator has mouse clicked on bars 622A–622F, which has caused them to turn green. By clicking on bars 622A–622F, the operator has selected corresponding micro-well plates 125A–125F to "run". The operator sends the command to run the selected micro-well plates by clicking on run bar 623.

Figure 8:
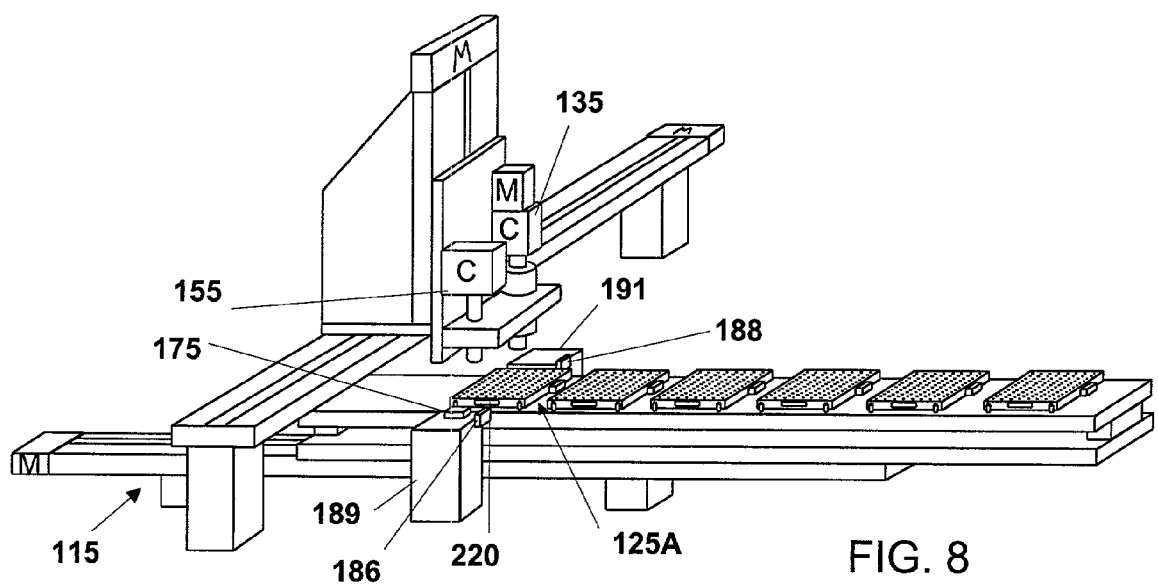
FIGS. 8–10 and 18–25 show steps in the sequence of operations of a preferred embodiment of the present invention.

In FIG. 8, the operator has given the command to run the selected micro-well plates. Micro-well plate 125A has been moved to a position underneath cameras 155 and 135. By the utilization of plate sensor transmitter/receiver 186 and reflector 188, information is sent to computer 105 reporting that micro-well plate 125A is in position underneath the cameras. Plate sensor transmitter/receiver 186 is fixed to support 189 and is aligned to sense whenever a micro-well plate breaks a beam of light emitted by transmitter/receiver 186 and reflected by a reflector 188. Reflector 188 is mounted on support 191 on the opposite side of the linear actuator 115. The plate sensor transmitter/receiver 186 and reflector 188 are preferably model # E3T-SR13 available from Western Switch Controls of Santa Ana, Calif.

Bar code reader 175 is also mounted to support 189 and is positioned to view bar-code identity label 220 (FIG. 2) attached to micro-well plate 125A when it is positioned underneath cameras 155 and 135. Bar-code reader 175 is preferably model # BL601 available from Keyence Corporation of America of Newark, N.J. Bar-code reader 175 communicates with computer 105 via a communication line. Information encoded into label 220 preferably includes: the plate serial number, the plate type (i.e., 24-well, 48-well, 96-well, 384-well, or 1536-well micro-well plate), and the well type (i.e., square, or rounded, hanging drop, sitting drop, constrained sitting drop).

The information from plate sensor transmitter/receiver 186 and bar-code reader 175 is transmitted to computer 105 and stored for later use during the camera inspection and information acquisition phase.

Figure 9:
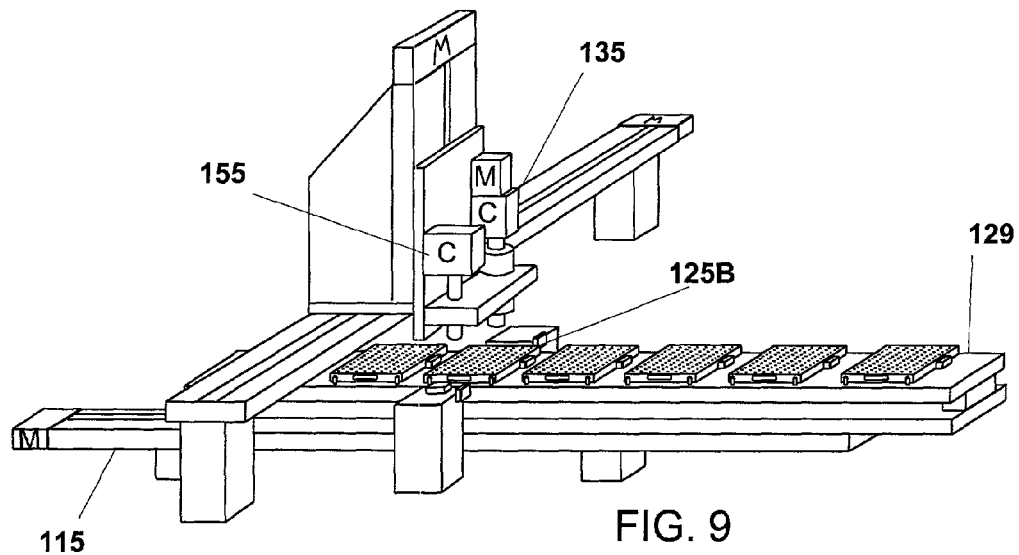

In FIG. 9, linear actuator 115 has moved fixture plate 129 so that micro-well plate 125B is underneath cameras 155 and 135. In a fashion similar to that described above with regards to micro-well plate 125A, information is transmitted from plate sensor transmitter/receiver 186 and bar-code reader 175 to computer 105 and stored for later use during the camera inspection and information acquisition phase.

The above described sequence continues until all micro-well plates 125A–125F have been sensed and recorded by plate sensor transmitter/receiver 186 and bar-code reader 175.

Figure 10:
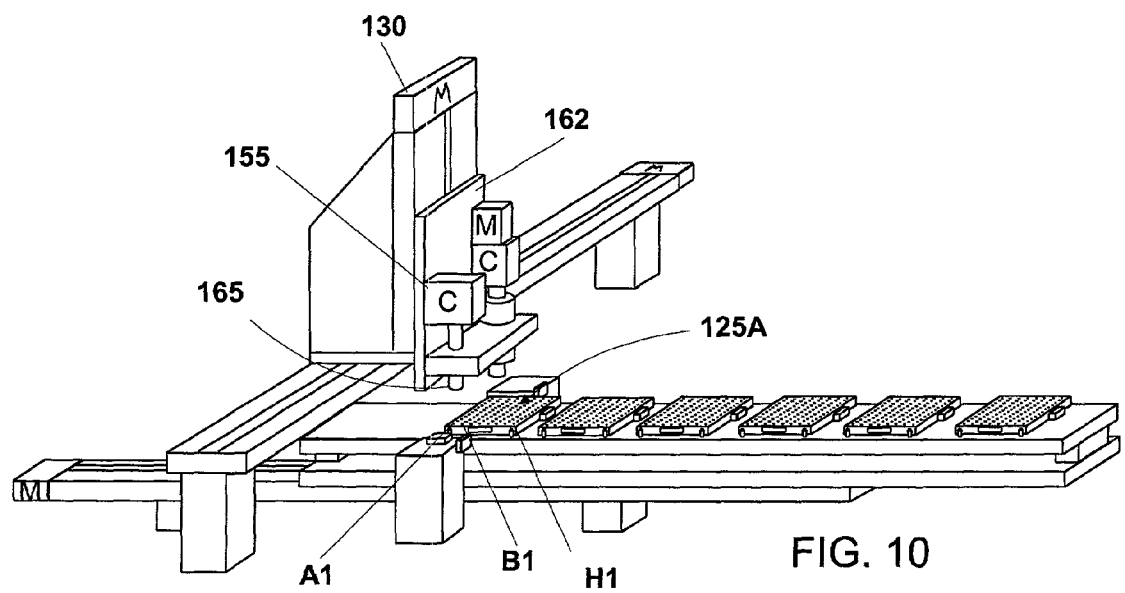

Then, as shown in FIG. 10, linear actuator 115 moves micro-well plate 125A so that it is underneath lens 165 of camera 155. Motor 130 of linear actuator 160 moves moving plate 162 upward and/or downward as necessary to properly focus lens 165 on the drop of hanging liquid over well A1. Preferably, lens 165 is set at a predetermined zoom.

Inspection of Crystals Determining the Position of the Drop of Liquid within Each Well An operation to inspect each well to determine the position of each hanging drop of liquid is performed on micro-well plate 125A after it has been moved to the position shown in FIG. 10.

Figure 11:
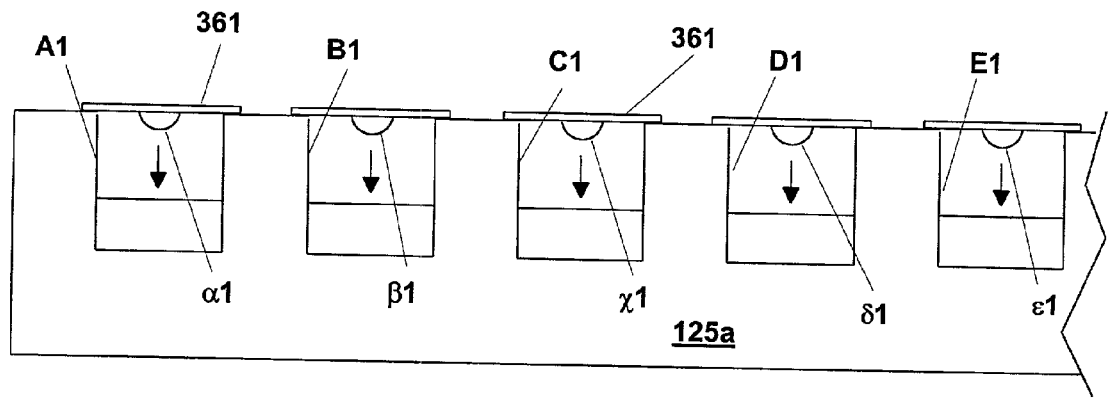
FIG. 11 shows hanging drops of liquid in a micro-well plate.

FIG. 11 shows a cross section side view of wells A1–E1 of micro-well plate 125A. In a preferred embodiment, an attempt has been made to grow protein crystals in the hanging drops in each of the wells of micro-well plate 125A. FIG. 11 shows hanging drops $\alpha 1$, $\beta 1$, $\chi 1$, $\delta 1$, and $\epsilon 1$.

The preferred method for protein crystal growth is the hanging drop method. The hanging drop method (also known as vapor diffusion) is probably the most common method of protein crystal growth. As explained in the background section, a drop of protein solution is suspended over a reservoir containing buffer and precipitant. Water diffuses from the drop to the solution leaving the drop with optimal crystal growth conditions.

Figure 13:
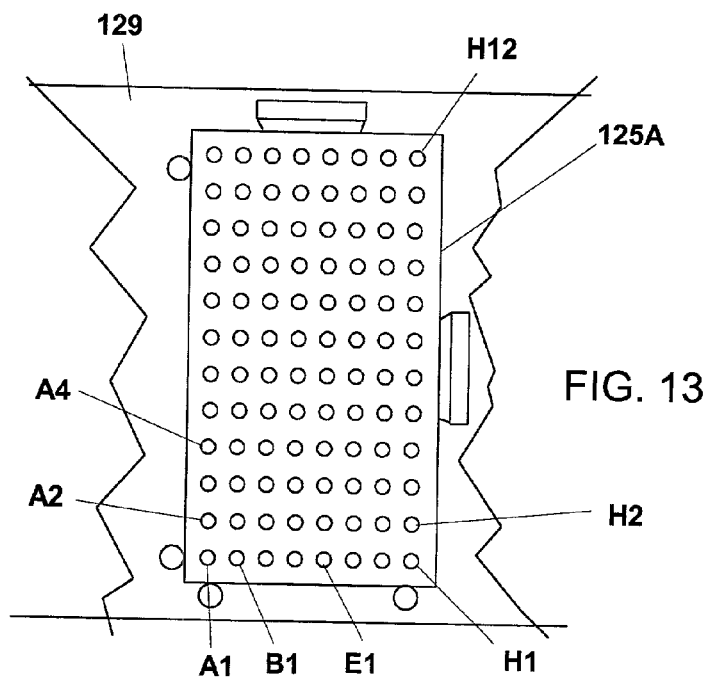
FIG. 13 shows a top view of a micro-well plate on the fixture plate.

In FIG. 10, lens 165 of camera 155 is over well A1 of micro-well plate 125A (FIG. 2, FIG. 11, and FIG. 13). FIG. 13 shows a top view of micro-well plate 125A positioned on fixture plate 129.

FIG. 14 shows a side view of micro-well plate 125A positioned on fixture plate 129. Support 191 with embedded light source 194 is positioned to the side of fixture plate 129. Light from light guide 195 is directed upward through cutout 131 (also shown in FIG. 3). Light guide 195 is positioned between fixture plate 129 and plate 127 such that both plates can move around the light guide 195 without interference. As explained above, fixture plate 129 has cutouts 131 (FIG. 3) that are smaller than the micro-well plates 125 and located under each well plate, such that light from light guide 195 can be projected through the well plates when they are brought into position for inspection. In the preferred embodiment, light source 194 is model # A08925 fiber-optic backlight available from Aegis Electronics of Carlsbad, Calif.

Camera 155 (FIG. 10) inspects well A1 and transmits an image to computer 105 for digitization. As described above, camera 155 preferably (FIG. 10) inspects well A1 at a 1× magnification so that every 6.7 micron square pixel represents approximately 6.7 square microns on the object being measured, allowing for some small geometric distortions caused by the lens 165. Computer 105 has been programmed to digitize the camera image and then by utilizing vision software determines a position within well A1 for the drop of liquid hanging from grease seal 361. The position of the drop of liquid is recorded for later use onto the hard drive of computer 105 and to a memory location within the computer.

In a preferred embodiment, the vision software used to determine the position of the drop of liquid uses a software routine algorithm called mvt_blob_find from a collection of image processing tools called MVTools. MVTools is available from Coreco Imaging, US Office in Bedford, Mass.

After recording the position of the drop of liquid hanging from grease seal 361 in well A1, linear actuator 115 moves fixture plate slightly to the left so that lens 165 is over well B1 (FIG. 13). In a fashion similar to that described for well A1, the position of the drop of liquid hanging from grease seal 361 in well B1 is recorded on the hard drive of computer 105 and in computer memory. For example, as shown in FIG. 15, computer 105 will record that drop of liquid $\alpha 1$ is towards the upper left-hand quadrant of well A1. Likewise, the position of drop of liquid $\beta 1$ is recorded onto the database of computer 105 as being in the lower right-hand quadrant of well B1.

Figure 18:
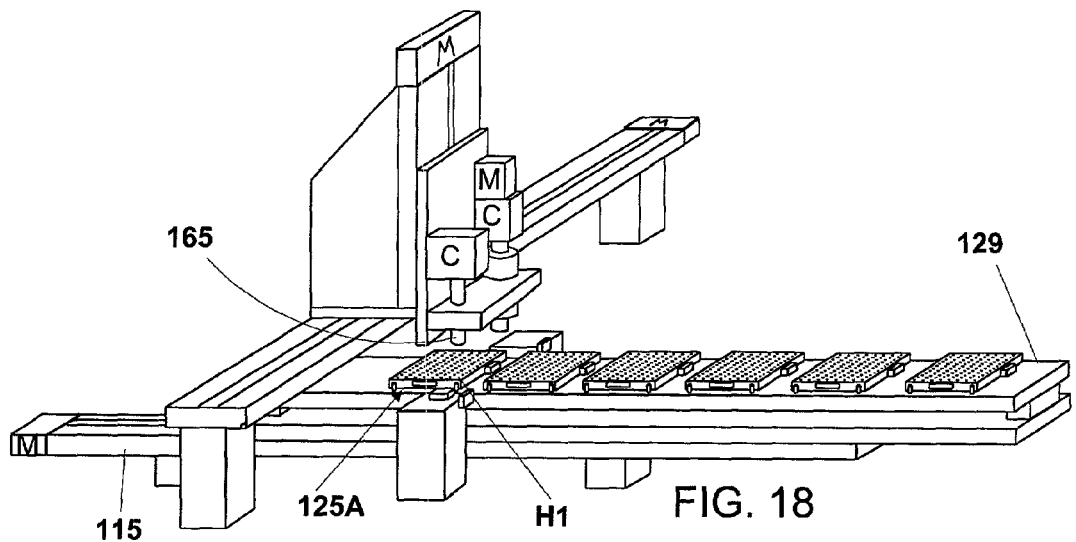

In this manner, positions of the drops of liquid are recorded for cells A1–H12. In FIG. 18, linear actuator 115 has moved fixture plate 129 so that well H1 is under lens 165.

Figure 19:
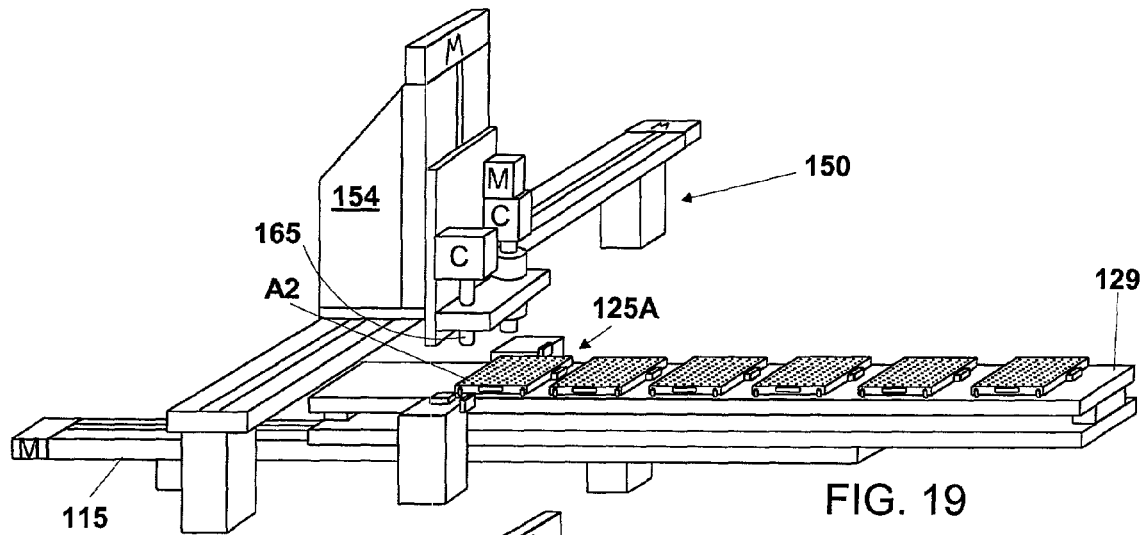

In FIG. 19, linear actuator 115 has moved fixture plate 129 to the left and linear actuator 150 has moved moving base 154 slightly rearward so that lens 165 is over well A2 of micro-well plate 125A (FIG. 13).

Figure 20:
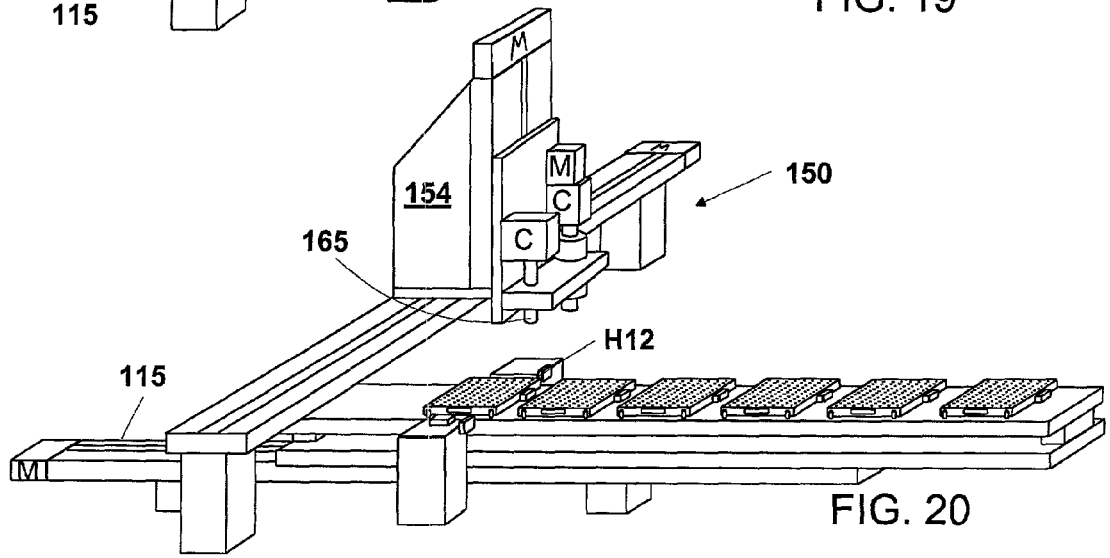

In a manner similar to that described above, positions of the drops of liquid are recorded for cells A2–H12 (FIG. 2, FIG. 13). In FIG. 20, linear actuator 115 has moved fixture plate 129 to the left and linear actuator 150 has moved moving base 154 rearward so that well H12 is under lens 165.

Figure 21:
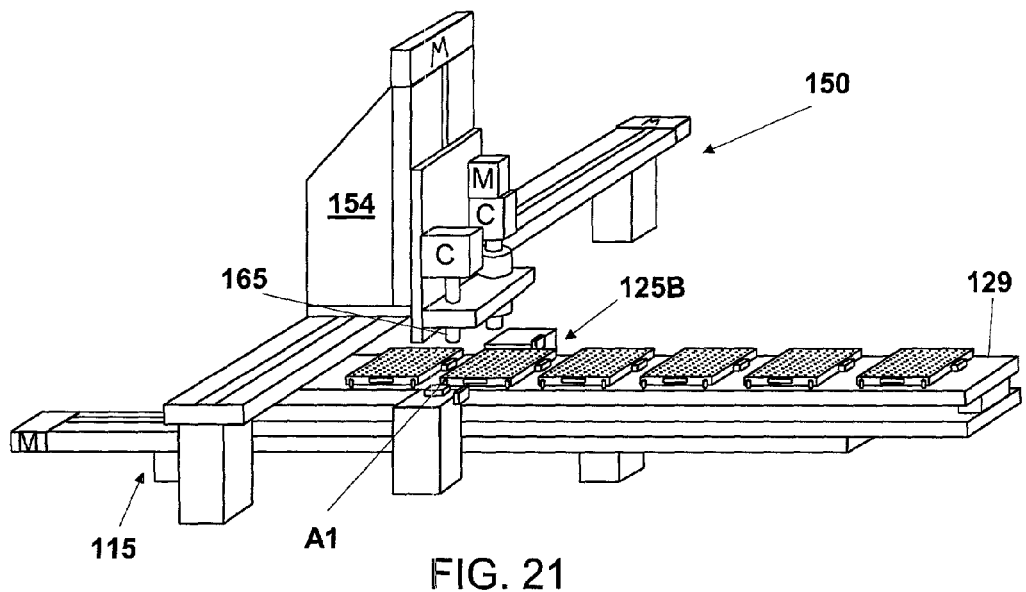

After positions of the drops of liquid are recorded for cells A1–H12 for micro-well plate 125A, linear actuator 115 moves fixture plate 129 and linear actuator 150 moves moving base 154 so that cell A1 of micro-well plate 125B is underneath lens 165 (FIG. 21).

Figure 22:
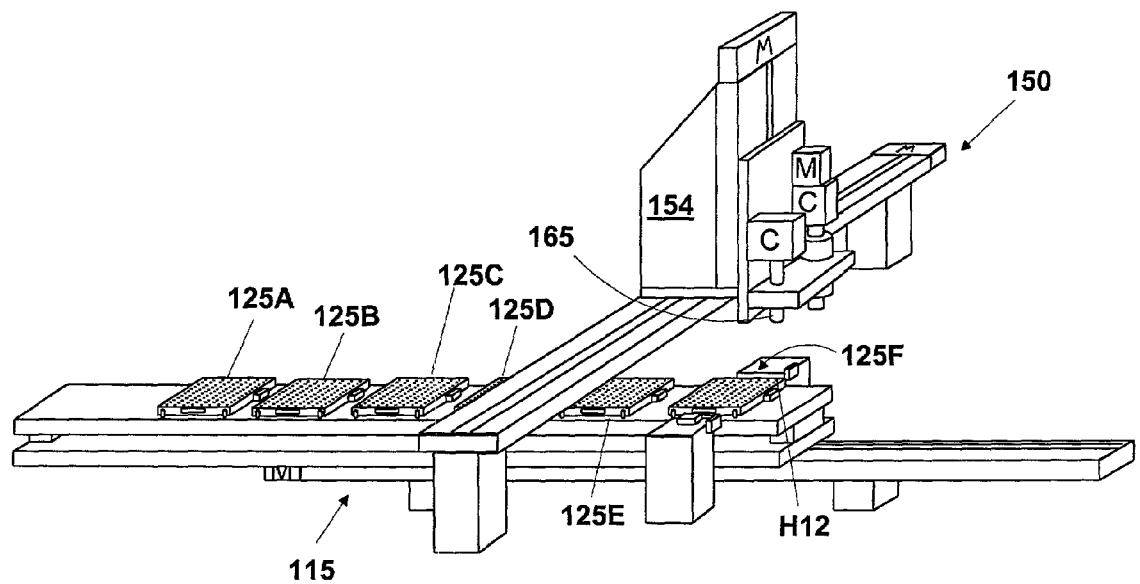

In a manner similar to that described above, positions of the drops of liquid are recorded for cells A1–H12 for each micro-well plate 125A–125F. In FIG. 22, linear actuator 115 has moved fixture plate 129 and linear actuator 150 has moved moving base 154 so that well H12 of micro-well plate 125F is under lens 165.

Recording the Image of the Drop of Liquid within Each Well

Figure 23:
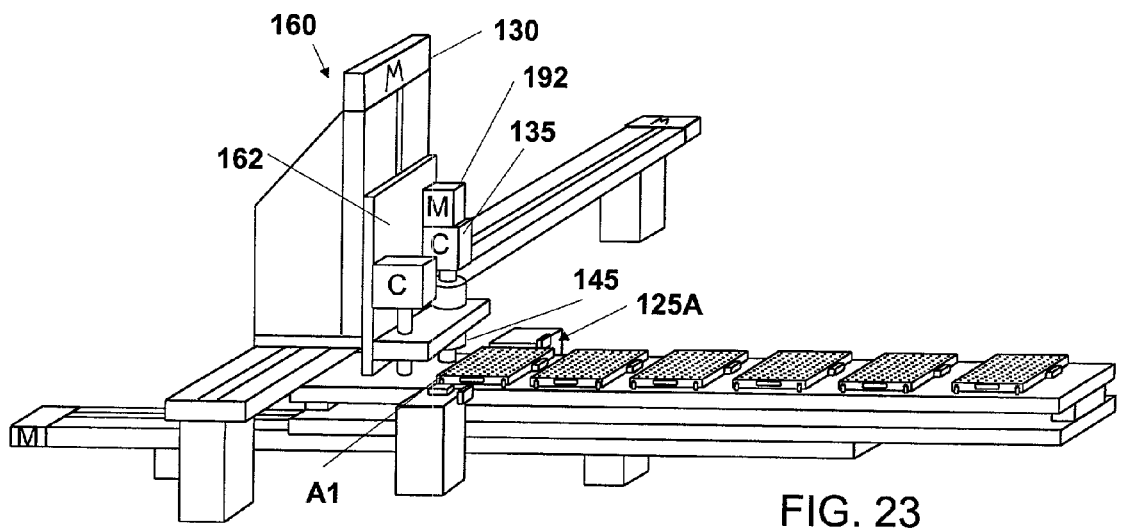

An operation to inspect each hanging drop is performed at a higher magnification using camera 135 with its zoom lens 145 capable of magnifications of 2.5× to 10× corresponding approximately to digitized pixels representing 2.68 microns square (at 2.5×) to 0.67 microns square (at 10×). This inspection is done for the purpose of determining whether protein crystals have grown. Zoom motor 192 controls the degree of zoom for zoom lens 145. Using data representing the position of the drop of liquid within each well obtained during the inspect-well sequence, computer 105 (FIG. 1) automatically transmits a signal to linear actuators 115 and 150 to position lens 145 directly over the drop of liquid within each well. For example, in FIG. 23 lens 145 is positioned over the top of well A1 of micro-well plate 125A. Using the positioning data earlier obtained, lens 145 is precisely positioned so that it is able to zoom in on drop of liquid α1 (FIG. 13). FIG. 16 shows a magnified view of drop of liquid α1. In FIG. 23, motor 130 of linear actuator 160 has moved moving plate 162 upward and/or downward as necessary to properly focus lens 165 on drop of liquid α1. Zoom motor 192 has manipulated lens 165 to obtain the desired degree of zoom. Camera 135 inspects well A1 and transmits a signal representing the magnified image of the hanging drop of liquid to computer 105. The images are stored on computer 105 temporarily in memory for immediate analysis and on hard disk for later analysis.

In a similar fashion, linear actuators 115, 150 and 160 and zoom motor 192 operator to properly position and magnify zoom lens 145 over each hanging drop of liquid to obtain desired focus and magnification for image data storage. For example, FIG. 17 shows a magnified view of hanging drop of liquid β1.

Figure 24:
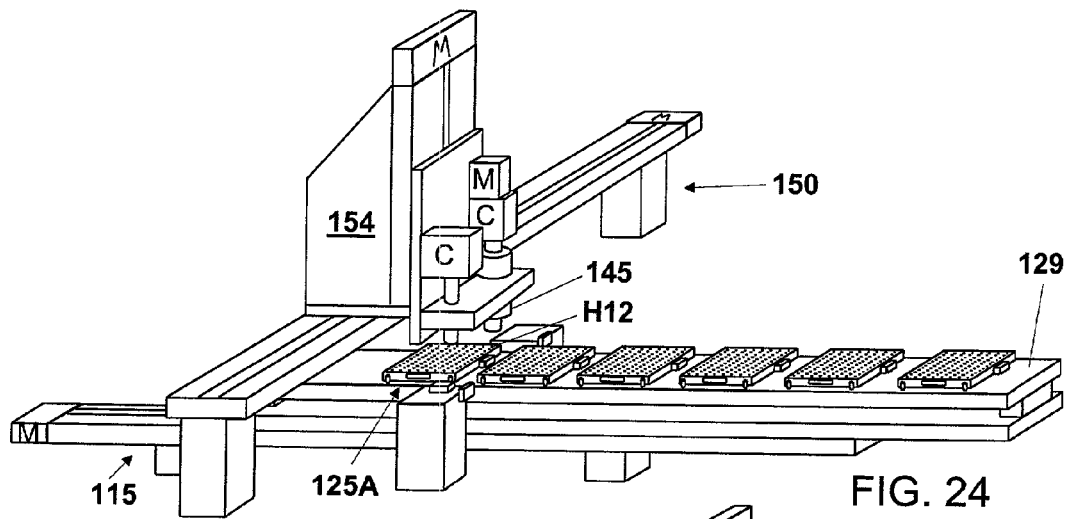

In a manner similar to that described above during the inspect-well sequence, magnified images of the drops of liquids (similar to those shown in FIGS. 16 and 17) are recorded for cells A1–H12 for micro-well plate 125A (FIG. 2, FIG. 13). In FIG. 24, linear actuator 115 has moved fixture plate 129 and linear actuator 150 has moved moving base 154 so that well H12 of micro-well plate 125A is under lens 165.

Figure 25:
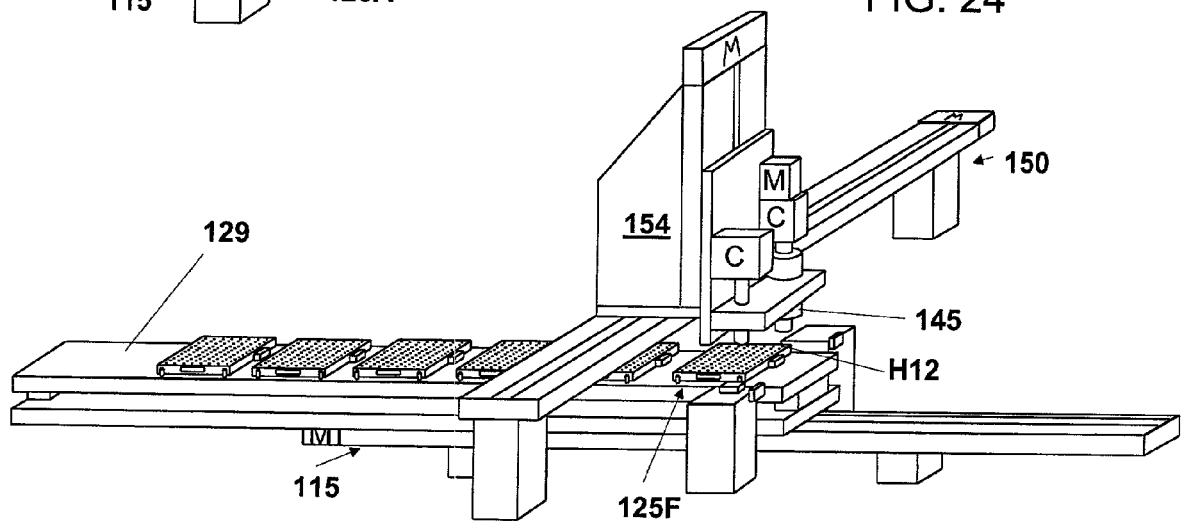

Then, the sequence is repeated for micro-well plates 125B–125F so that magnified images of the hanging drops of liquids are recorded for each cell A1–H12 for micro-well plates 125B–125F. In FIG. 25, the sequence has ended for micro-well plates 125A–125F. Linear actuator 115 has moved fixture plate 129 and linear actuator 150 has moved moving base 154 so that well H12 of micro-well plate 125F is under lens 145.

Manual Scoring the Drop of Liquid within Each Well

After micro-well plates 125A–125F have been run, monitor 620 will appear as shown in FIG. 26. In FIG. 26, six images representing micro-well plates 125A–125F appear on the screen. Above each image is a message "Run Comp" indicating that image data for hanging drops of liquid has been transferred into computer 105. Beneath each image are buttons 710–715 marked "S". By mouse clicking on any button 710–715, the operator may manually score for successful crystal formation each magnified image of each hanging drop of liquid.

For example, in FIG. 26, the operator can mouse click on button 710 to score micro-well plate 125A.

In FIG. 27, the operator has mouse clicked on the circle representing well A1 of micro-well plate 125A. This has caused a magnified image to be displayed of drop of liquid α1 in screen section 716. The operator has concluded that there are no crystals in drop of liquid α1 and has therefore mouse clicked on button 717 for "NO CRYSTAL". On the display screen, this has caused the circle representing well A1 of micro-well plate 125A to turn red.

Figure 28:
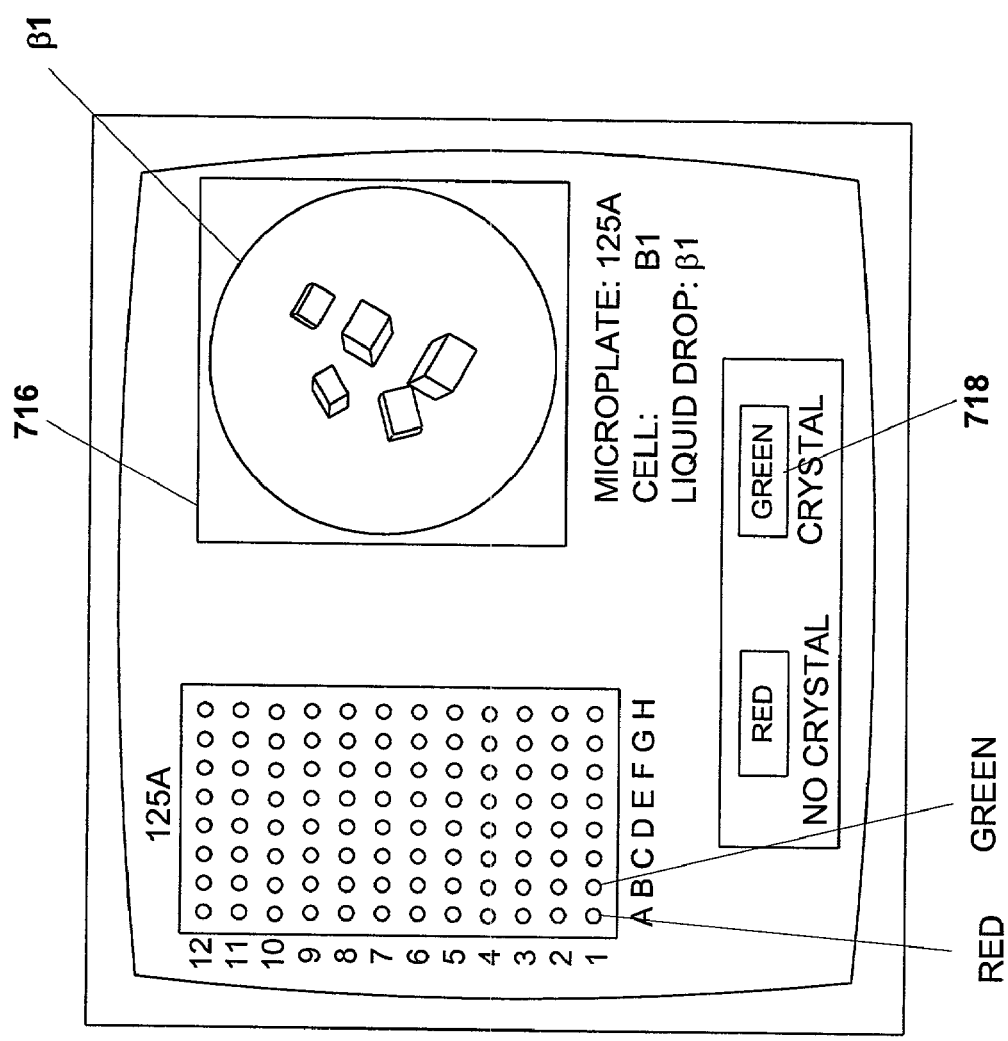

In FIG. 28, the operator has mouse clicked on the circle representing well B1 of micro-well plate 125A. This has caused a magnified image to be displayed of drop of liquid β1 in screen section 716. The operator has concluded that there are crystals in drop of liquid β1 and has therefore mouse clicked on button 718 for "CRYSTAL". On the display screen, this has caused the circle representing well B1 of micro-well plate 125A to turn green.

In a similar fashion, the above scoring procedure is repeated until all wells A1–H12 for micro-well plates 125A–125F have been scored as either red (NO CRYSTAL) or green (CRYSTAL).

Data Utilization

Once micro-well plates 125A–125F have all been scored, the operator has at his easy disposal a database that contains the identity of each micro-well plate that was inspected along with a score summarizing whether crystal formation occurred for each well in the micro-well plate. The automated and efficient manner in which the operator is able to acquire his contrasts with the prior art method of laboriously inspecting each well with a microscope and the handwriting the results into a notebook.

For example, to score six 96-well micro-well plates utilizing the present invention should take approximately no more than 10 to 15 minutes.

In contrast, the prior art method of inspecting six 96-well micro-well plates with a microscope and the handwriting the results into a notebook will take approximately 30 to 100 minutes depending on the conditions discussed in the background section in addition to the time required to transcribe the results into a computer database. Plus, as previously explained in the background section, manual inspection and scoring is subject to a relatively high risk of human error.

Second Preferred Embodiment

Figure 29:
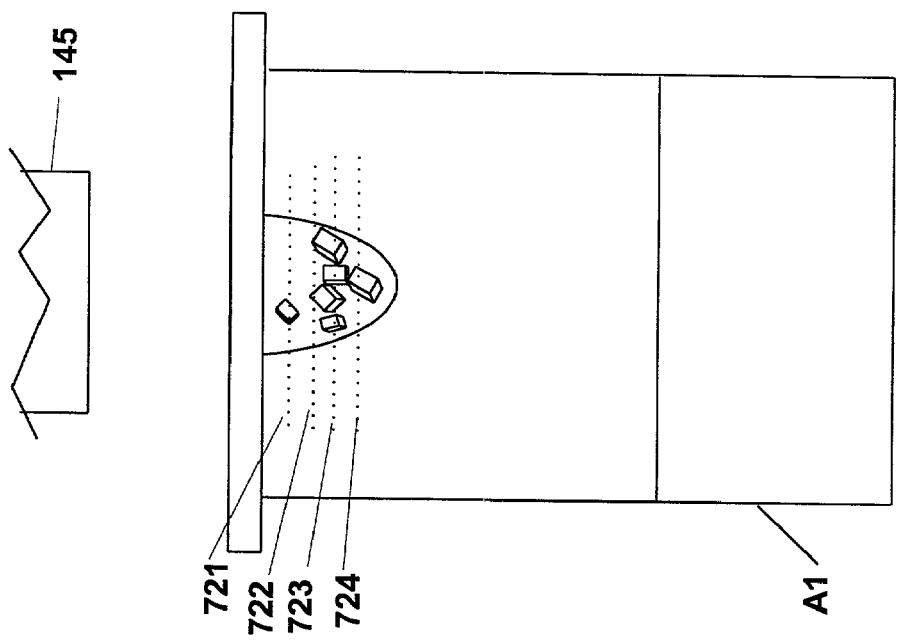
FIG. 29 shows a hanging drop of liquid with crystal growth.

In a second preferred embodiment, the depth of view of camera 135 is approximately 50 to 100 micrometers. The crystal in the drop of liquid may be larger than the depth of view or there may be crystals growing at various levels within the hanging drop of liquid, as shown in FIG. 29. Therefore, in the second preferred embodiment, lens 145 is focused at multiple different levels 721–724 and a set of images are recorded at the different levels so that the entire crystal may be analyzed.

Specimen Auto-Focus

Figure 31:
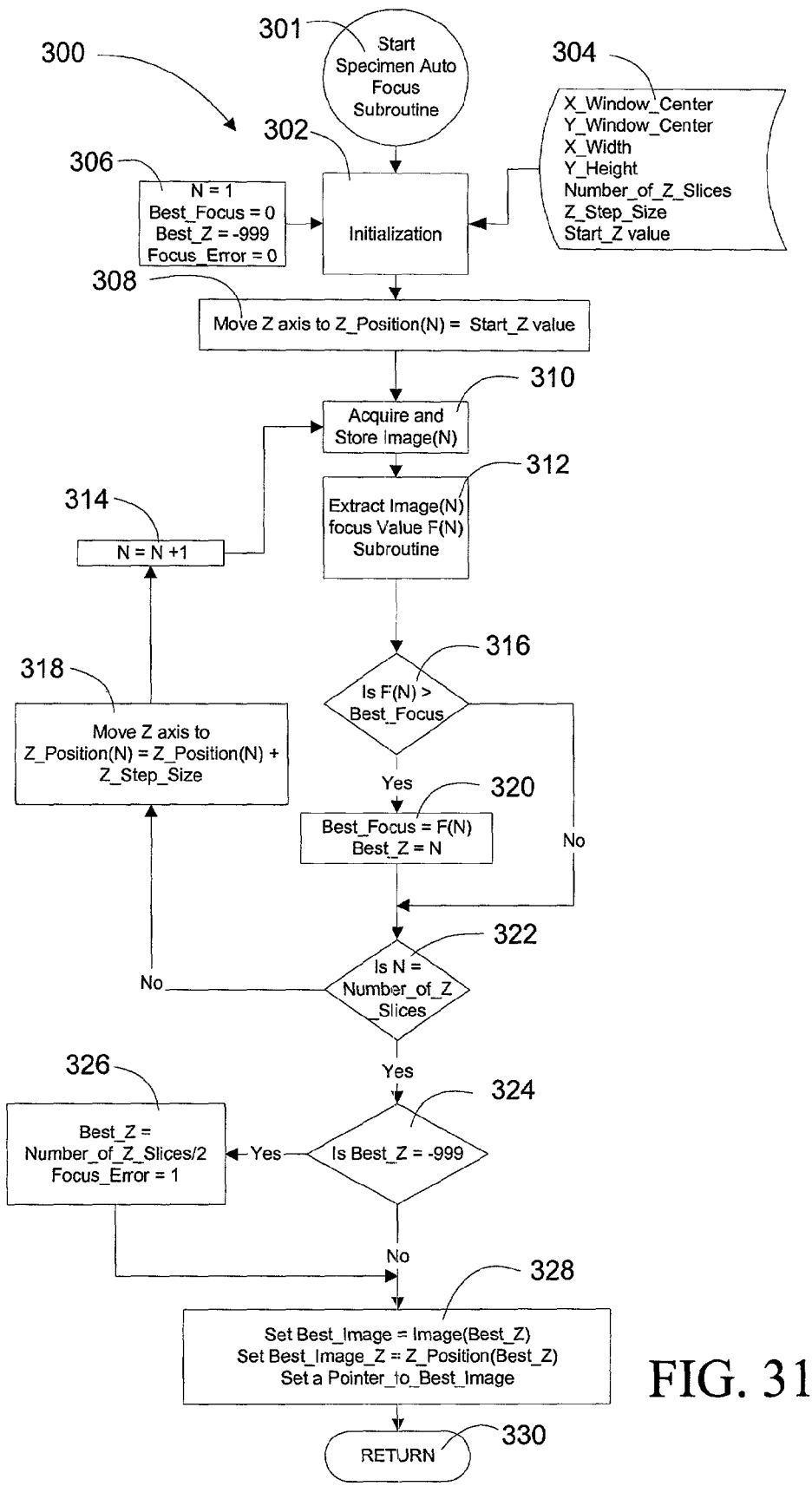
FIG. 31 shows a flowchart of an auto-focus subroutine of the present invention.

The third preferred embodiment of the present invention utilizes a specimen auto-focus subroutine 300 (FIG. 31). Subroutine 300 ensures that the specimen within the micro-well is in-focus at the desired zoom (or magnification ratio) of image lens 145. Utilizing the auto-focus feature, the present invention causes camera 135 to take a number of images defined by a Number_of_Z_Slices. Typically, there are between 5 and 10 slices separated in the Z-axis from one another by a Z_Step_Size. The typical step size is 0.05 mm to 0.25 mm. The slices preferably start at a Z-Axis location defined by a Start_Z value, which is typically at the bottom of the cover-slip on the micro-well plate. During specimen auto focus initialization 302, input data 304 is received. The area of interest window within the images is further defined in the input data 304 by a X_Window_Center and a Y_Window_Center plus an X_Width and a Y_Width. Initial settings 306 for the routine 300 are the starting value of a counter N, a Best_Focus, a Best_Z, and a Focus_Error. The inspection device sets Z_Position(N) equal to the Start_Z location and moves camera 135 there in step 308. An image is acquired with camera 135 and digitized as previously described and stored as Image (N) in step 310. A second subroutine 312 extracts a focus value F (N) for Image (N) and is further described in the section for discussion for FIG. 32. A test is made between F(N) and the Best_Focus in step 316, such that if F(N) is greater than Best_Focus then Best_Focus is set to F(N) and Best_Z is set to N as shown in step 320 and the program flow goes onto step 322, if the test condition is not met in step 316 then the program flow skips step 320 and goes on to step 322. In step 322, a test is made to determine of all of the slices have been taken as N is tested against the Number_of_Z_Slices. If N is equal to Number_of_Z_Slices then program flow goes onto step 324. If more slice images are needed, then the flow goes to step 318. In step 318, Z_Position(N+1) is set to Z_Position(N)+Z_Step_Size and the Z-Axis is moved to Z_Position(N+1) and the program flow goes on to step 314 where N is incremented by 1 (one). The program flow goes back to step 310 and completes the loop of step 310 to step 322 until all of the image slices have been taken and then moves onto step 324. In step 324, Best_Z is tested against its initial value, and if it equals its initial value (meaning no focus was found in the focus value subroutine 312) then it is set to a default value of the Number_of_Z_Slices divided by 2 and Focus_Error is set to 1 (one) in step 326 and the program flow goes onto step 328. If Best Z in step 324 has a value other than its initial value then program flow goes onto step 328 from step 324. In step 328 a Best_Image image is set to the image slice at best focus by setting Best_Image equal to Image(Best_Z). Also, a Best_Image_Z value is set equal to Z_Position(Best_Z) and the flow goes onto step 330 which is the RETURN part of the subroutine and program flow returns to the main software flow.

Figure 32:
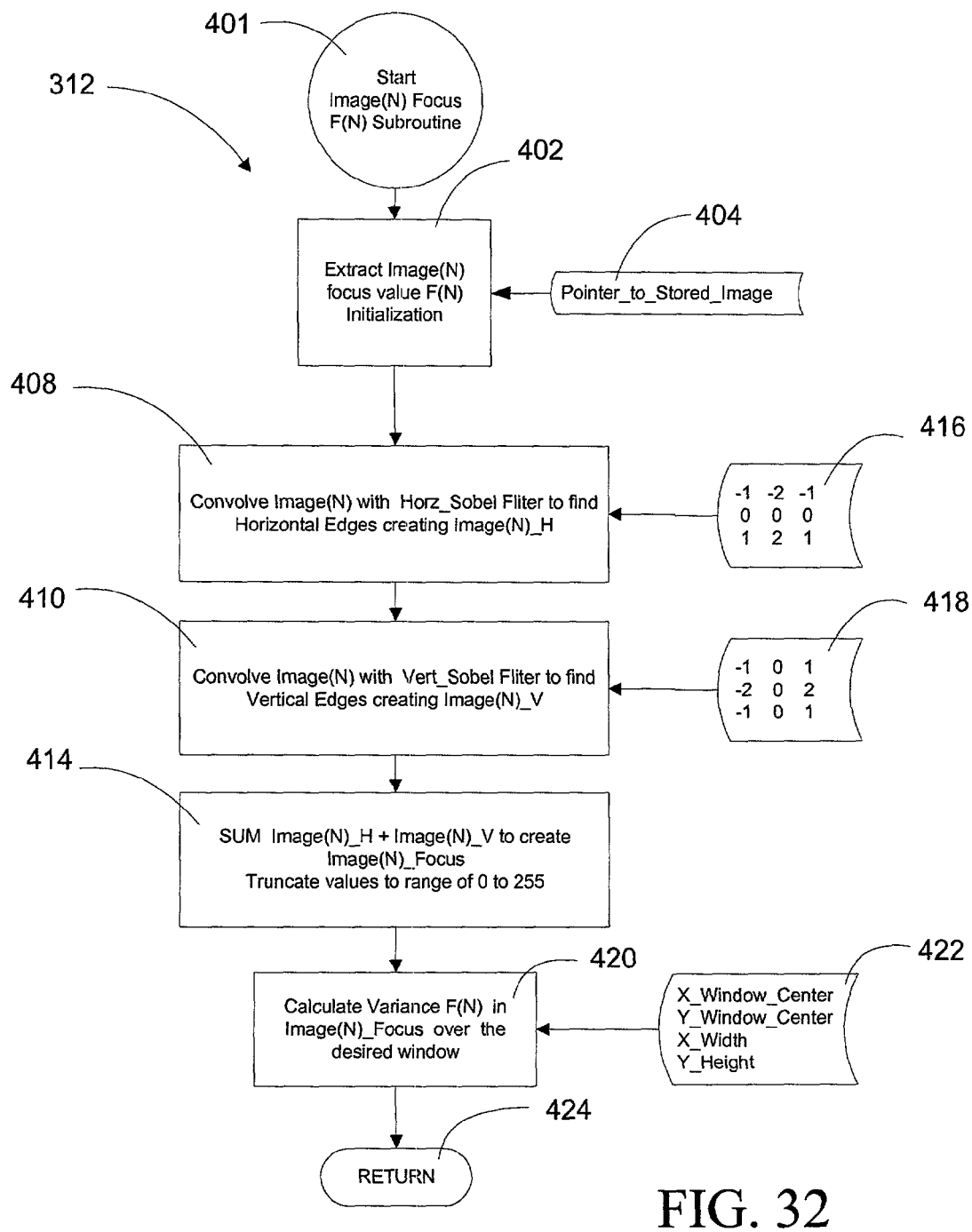
FIG. 32. shows a flowchart of a focus value subroutine.

As illustrated in FIG. 32. an image(N) focus F(N) subroutine 312 is further detailed, starting at the step Start 401. A pointer_to_image(N) 404 is provided in step 402. In step 408 the image(N) is convolved with a standard 3×3 Sobel_Horizontal filter 416 to produce an Image(N)_H wherein horizontal edges within the image are emphasized. In step 410 the image(N) is convolved with a standard 3×3 Sobel_Vertical filter 418 to produce an Image(N)_V wherein vertical edges within the image are emphasized. In step 414, both the horizontal edge emphasized image Image(N)_H and the vertical edge emphasized image Image(N)_V are summed pixel by pixel, during the summing process any resulting negative pixel values are set to zero and any resulting pixel values that are greater than 255 are set to 255, to produce an image Image(N)_Focus. In step 420, a simple variance F(N) is calculated for the pixels within a window of interest defined in 422 by X-Window_Center, Y_Window_Center, X_width, and Y_Height. The resulting value of the variance is returned to the calling program as F(N) in step 424. The sobel processing and the variance calculation is performed with a collection of image processing software tools within MVTools. MVTools is available from Coreco Imaging, US Office in Bedford, Mass.

Fourth Preferred Embodiment

In the first preferred embodiment, it was disclosed how an operator could manually score each drop of liquid as either "CRYSTAL" or "NO CRYSTAL". In the fourth preferred embodiment, the operator is given a greater variety of options in deciding on how to score each drop. Table 1 shows listing of the operator's scoring options, including number, text description, and the corresponding color code. Once a micro-well drop has been scored a 9, the operator can further classify the crystals in a scoring shown in Table 2.

TABLE 1

| SCORE | DESCRIPTION | DISPLAY COLOR |
| --- | --- | --- |
| 0 | clear | White |
| 1 | light precipitation | Red |
| 2 | heavy precipitation | Yellow |
| 3 | ugly precipitation | Blue |
| 4 | phase separation | Orange |
| 5 | unknown | Violet |
| 6 | Spherolites | Black |
| 7 | Grainy precipitation | Gray |
| 8 | Microcrystals | Brown |
| 9 | Crystal | Green |

TABLE 2

| SCORE | DESCRIPTION |
| --- | --- |
| 9.0 | crystal (no comments) |
| 9.1 | needles, intergrown |
| 9.2 | needles, single |
| 9.3 | plates, intergrown |
| 9.4 | plates, single |
| 9.5 | chunks, <50 microns, intergrown |
| 9.6 | chunks, <50 microns, single |
| 9.7 | chunks, >50 microns, intergrown |
| 9.8 | chunks, >50 microns, single |
| 9.9 | gorgeous >50 microns |

Fifth Preferred Embodiment

In the forth preferred embodiment, it was disclosed how an operator can manually score each drop of liquid into one of 10 categories with corresponding color coding, and how the operator score category 9 into further subcategories of 9.0 through 9.9. In the fifth preferred embodiment, the inspection device automatically scores and classifies each drop specimen by executing computer software subroutines as shown in FIGS. 33, 34a, 34b, 34c, 34d, and 35a and 35b under control of the program flow shown in FIG. 36. The automatic classification can occur at three levels of detail, the first level, Type_of_Classification=1, simply discriminates between a drop that is clear or not-clear (unknown), the second level, Type_of_Classification=2, scores and classifies the drop into classes 0 through 9 as described in Table 1 above, and the third level, Type_of_Classification=3, performs second level scoring and classification, plus adds an additional 10 subcategories to the CLASS 9, crystal classification, as detailed in Table 2 above.

Automatic Scoring and Classification

Figure 36:
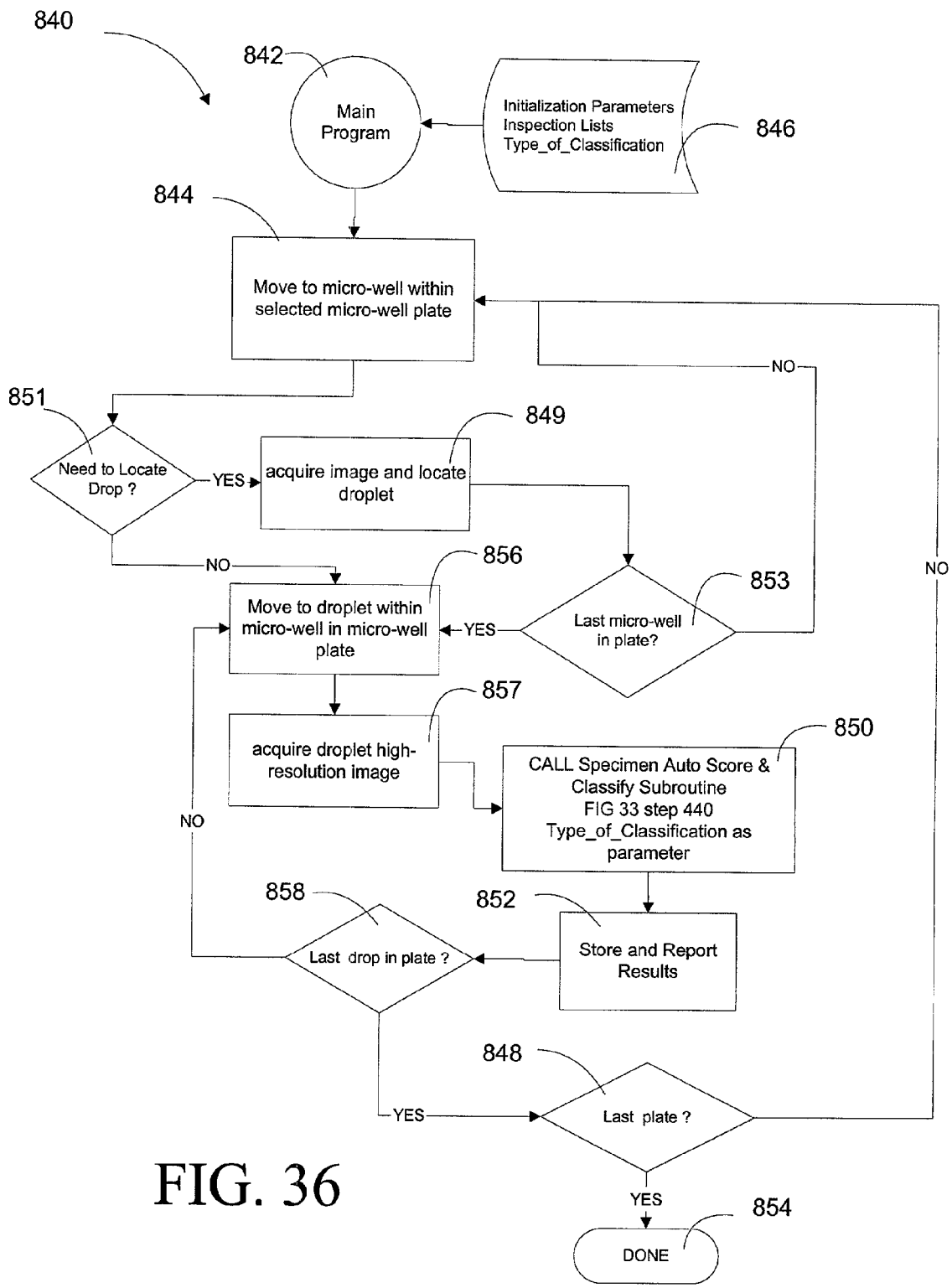
FIG. 36 shows the main program flow.

FIG. 36 illustrates the main program flow 840 starting at step 842. The software is initialized with parameters, inspection lists, and Type_of_Classification detailed in step 486. The flow continues onto step 844 where the system moves the micro-well of interest within the selected micro-well plate under the selected camera. In step 851, if the drop needs to be located, the flow continues onto step 849 wherein an image is acquired by the camera and software operates on the image and determines the location of the drop. Then a test is made to determine if the last micro-well in the plate has been imaged, if not then the flow loops to step 844 and continues. If the last micro-well in plate step 853 has been imaged then the flow continues to step 856 where the system moves to the droplet within micro-well in micro-well plate under the high-resolution camera. Also in step 851 if the drop had been previously located, then the flow would continue from step 844 directly to step 856 without the need to re-locate the drop. From step 856, the flow continues onto step 857 wherein a high-resolution image of the drop is obtained. Then the flow goes onto step 850. In step 850, a CALL is made to subroutine that automatically scores and classifies the drop depending on the Type_of_Classification required. The subroutine is detailed in FIG. 33 and starts at step 440 in FIG. 33. After the drop has been classified the subroutine returns to step 852 wherein the results are stored and reported. The program flow continues to step 858 where a test is made to determine if the last drop in the selected plate has been processed, if so then the flow goes onto step 848 wherein a test is made to determine if the last plate has been processed. If not, the flow loops back to 856 and continues. If the last plate has been processed, the flow goes onto step 854 and the program is done.

Figure 33:
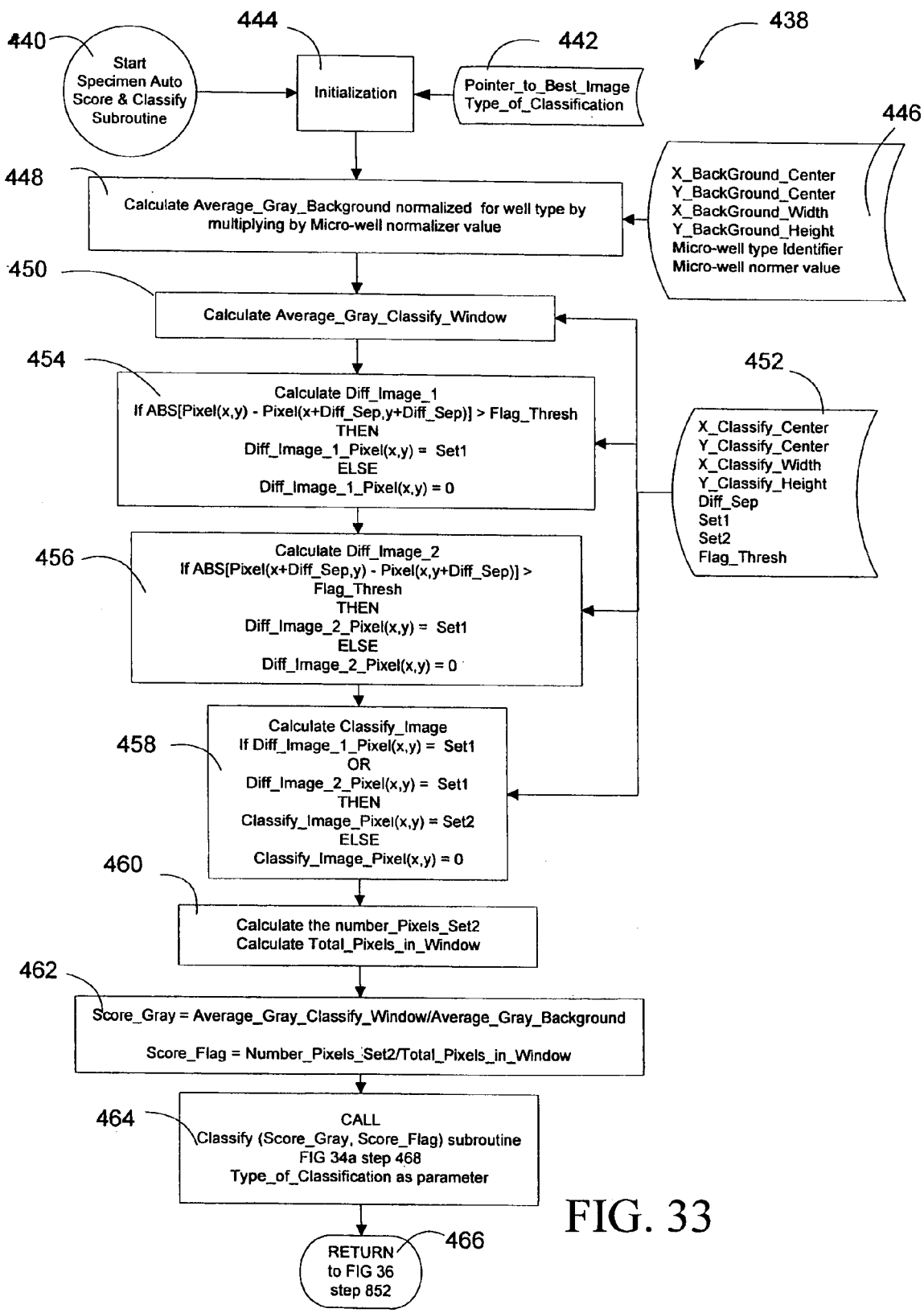
FIG. 33 shows a flowchart of the auto score and classify subroutine.

FIG. 33 shows Micro-well Specimen Auto Score and Classify Subroutine 438 starting at step 440. Pointer_to_Best_Image 442 provides information to the initialization step 444 that allows access to the image that was found to be the best focus. Plus, the Type_of_Classification is passed into the routine. Alternatively, pointer 442 can point to an image that was taken at a z height value known to be the focus of the system. After initialization 444 the subroutine 438 calculates in step 448 an average_gray_Background value normalized to allow for the variation present from various plate types, by using a first rectangular window defined by parameters shown in step 446 (X_Background_Center, Y_Background_Center, X_Background_Width, and Y_Background Height) and by summing all of the gray scale values of the pixels defined by the window 446 and dividing by the number of pixels within that window. The average_gray_background is normalized for well-type differences by multiplying the calculated value by a Micro-well normer value also found in step 446 and generally determined by measuring the various micro-well plate types under inspection and normalizing to the 96-well standard micro-well plate. This average_gray_background 448 is calculated in a window area of the image that is outside the area of the drop but generally within the well or within the bounding well walls.

In step 450 an average_gray_Classify_Window value is calculated in a similar manner as described above (except it is not normalized for micro-well type) using a second rectangular window defined by parameters shown in step 452 (i.e., X_Classify_Center, Y_Classify_Center, X_Classify_Width, and Y_Classify Height). This average_gray_classify_window value 450 is taken in a rectangular window area of the image that is inside the area of the drop and defined by being a fraction between 0.98 and 0.5 (with 0.8 preferred) of the width and height of the external bounding rectangular box from the blob utilizing subroutine mvt_blob_find. The subroutine mvt_blob_find defines the extent of the drop as previously discussed in the section "Determining the Position of the Drop of Liquid within Each Well".

In step 454, a diagonal difference image is calculated by stepwise subtracting pixel values from two pixel locations, defined by (x,y) and (x+Diff_Sep, y+Diff_Sep) within the Classify_window. The pixel values are separated in width and height by the value Diff_sep from step 452. This is repeated over all pixels within the Classify window defined by step 452 using X_Classify_Center, Y_Classify_Center, X_Classify_Width, and Y_Classify Height. For each value calculated the absolute value is taken of the subtraction result and compared to a threshold value Flag_Thresh defined in step 452. If the calculated value is greather than Flag_Thresh 452 then the pixel is set at the first location in x,y equal to a value defined by Set1 in step 452, if the calculated value is equal to or less than Flag_Thresh, 452, then the pixel value is set to zero. This can be seen by the mathematical equations and flow described in step 454 in calculating a Diff_Image_1. Typical values for Diff_Sep are between 1 to 20 pixels with 7 preferred. Typical values for Set1 are between 1 and 511 with 128 preferred. Typical values for Flag_Thresh are between 5 and 50 with 25 preferred.

In Step 456, a calculation similar to that performed in step 454 is performed on the Classify_Window except that the separation between the two pixels undergoing the calculation is defined by (x+Diff_Sep, y) and (x, y+Diff_Sep), as is shown in the mathematical calculation in 456 to generate a Diff_Image_2. This calculation uses definitions shown in step 452. Typical values for Set2 are between 1 and 511 with 200 preferred.

In Step 458 the Classify_Image, which is a combination of the images generated in step 454 and 456 is calculated as shown by the mathematical equations shown in step 458 using definitions shown in step 452. If the x,y pixel value in either Diff_Image_1 or Diff_Image_2 (steps 454 and 456 respectively) has a value equal to Set1 452 then the pixel value is set at (x,y) in Classify_Image equal to Set2 452. Otherwise, the value is equal to zero (0) as shown in the mathematical equations in step 458. The calculations are repeated for all pixels within the window defined in 452. The Classify_Image is basically an image of the classify_image_window wherein edges present within the original Best_Image are detected.

In step 460, the value of number_Pixels_Set2 is set equal to the total number of pixels that are set equal to Set2 452 in step 458. Also, the value of Total_Pixels_in_Window is set to the total number of pixels in the Classify_window in step 458.

In step 462, a Score_Gray is calculated by dividing the Average_Gray_Classify_Window determined in step 450 by the Average_Gray_Background found in step 448. A Score_Flag is also calculated by dividing the Number_Pixels_Set2 by Total_Pixels_in_Window from step 460. The Score_Gray and Score_Flag are normalized in this matter.

In step 464, the values of Score_Gray, Score_Flag, and Type_of_Classification are passed to a classify subroutine and a classification is returned for the Classify_image, effectively classifying the protein crystals within the window. Details of the Classify subroutine 464 are provided in FIGS. 34a, 34b, 34c, and 34d, plus FIGS. 35a and 35b.

Figure 34A:
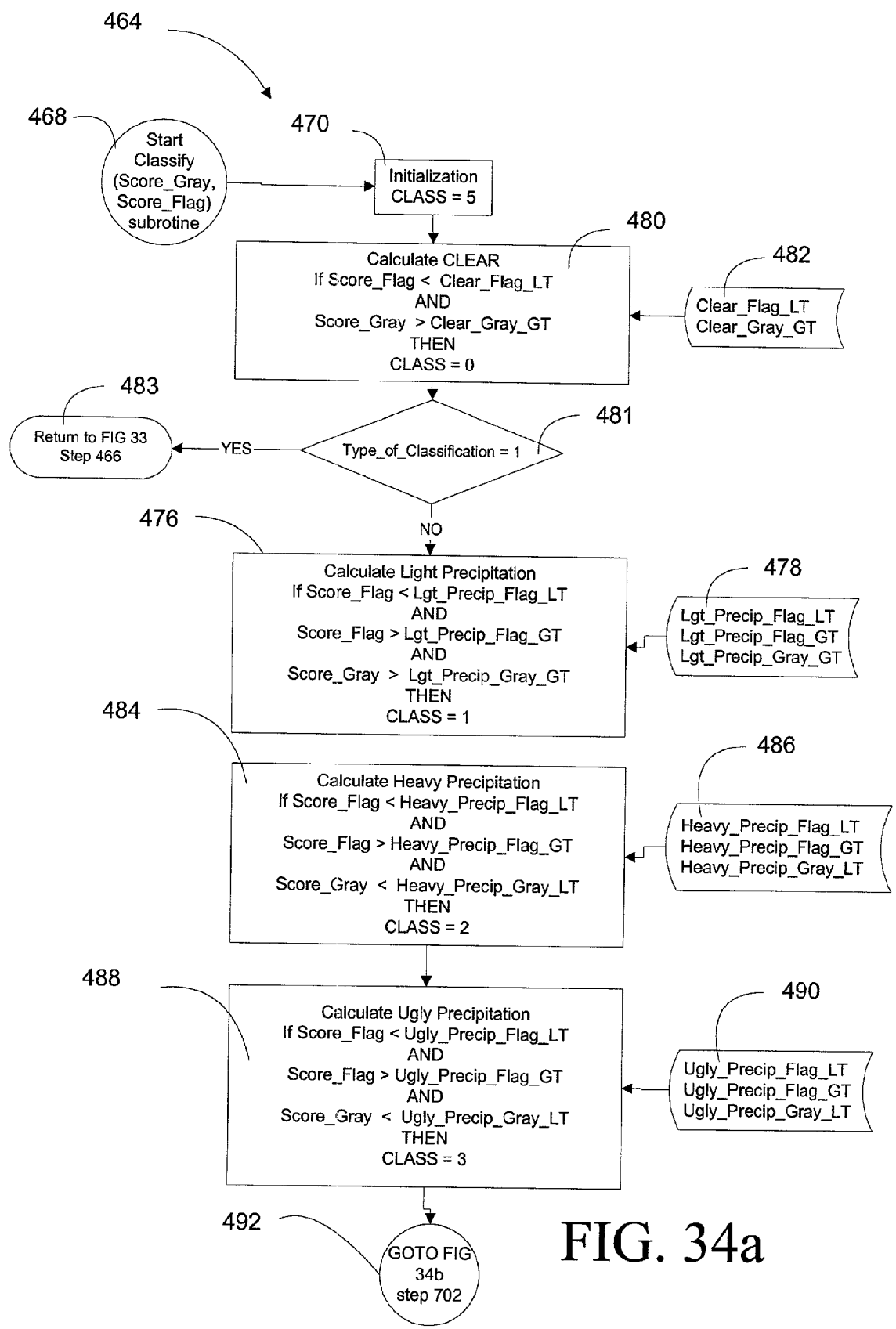
FIGS. 34a–34d show flowcharts of the classify subroutine.

FIG. 34a shows the Classify Subroutine 464. Start of Classify subroutine is shown in step 468 followed by initialization 470 whereby the initial classification CLASS value is set to 5, representing "unknown" and the flow goes onto step 480.

Step 480 calculates whether the drop is clear and the CLASS=0 by a test detailed in step 480 using thresholds defined in step 482 (Clear_Flag_LT and Clear_Gray_GT) with the following equation: if score_flag is less than Clear_Flag_LT and Score_Gray is greater than Clear_Gray_GT then set CLASS=0. At step 481, a test is made to see of the type_of_classification is equal to 1, the first classification type wherein the drop is classified as simply clear (0) or unknown (5) as previously discussed. If the type_of_classification is equal to 1 then the flow goes on to step 483 and then returns to FIG. 33 step 466 with the results. If the type_of_classification is not equal to 1 then the flow goes onto step 476 for further classification.

Step 476, utilizing threshold value parameters shown in step 478 (Lgt_Precip_Flag_LT, Lgt_Precip_Flag_GT, Lgt_Precip_Gray_GT), assigns the value of 1 to CLASS indicating that Light Precipitation is present in the Classify_Image. Step 476 utilizes the mathematical equation which states if Score_Flag is less than Lgt_Precip_Flag_LT and Score_Flag is greater than Lgt_Precip_Flag_GT and Score_Gray is greater than Lgt_Precip_Gray_GT then set CLASS to value 1.

Step 484 calculates heavy precipation by using thresholds detailed in step 486 (Heavy_Precip_Flag_LT, Heavy_Precip_Flag_GT, Heavy Precip_Gray LT) with the following equation: if score_flag is less than Heavy_Precip_Flag_LT and score_flag is greater than Heavy_Precip_Flag_GT and score_gray is less than Heavy Precip_Gray _LT then set CLASS=2.

Step 488 calculates ugly precipation by using thresholds detailed in step 490, Ugly_Precip_Flag_LT, Ugly_Precip_Flag_GT, Ugly_Precip_Gray_LT, with the following equation: if score_flag is less than Ugly_Precip_Flag_LT and score_flag is greater than Ugly_Precip_Flag_GT and score_gray is less than Ugly_Precip_Gray _LT then set CLASS=3.

Figure 34B:
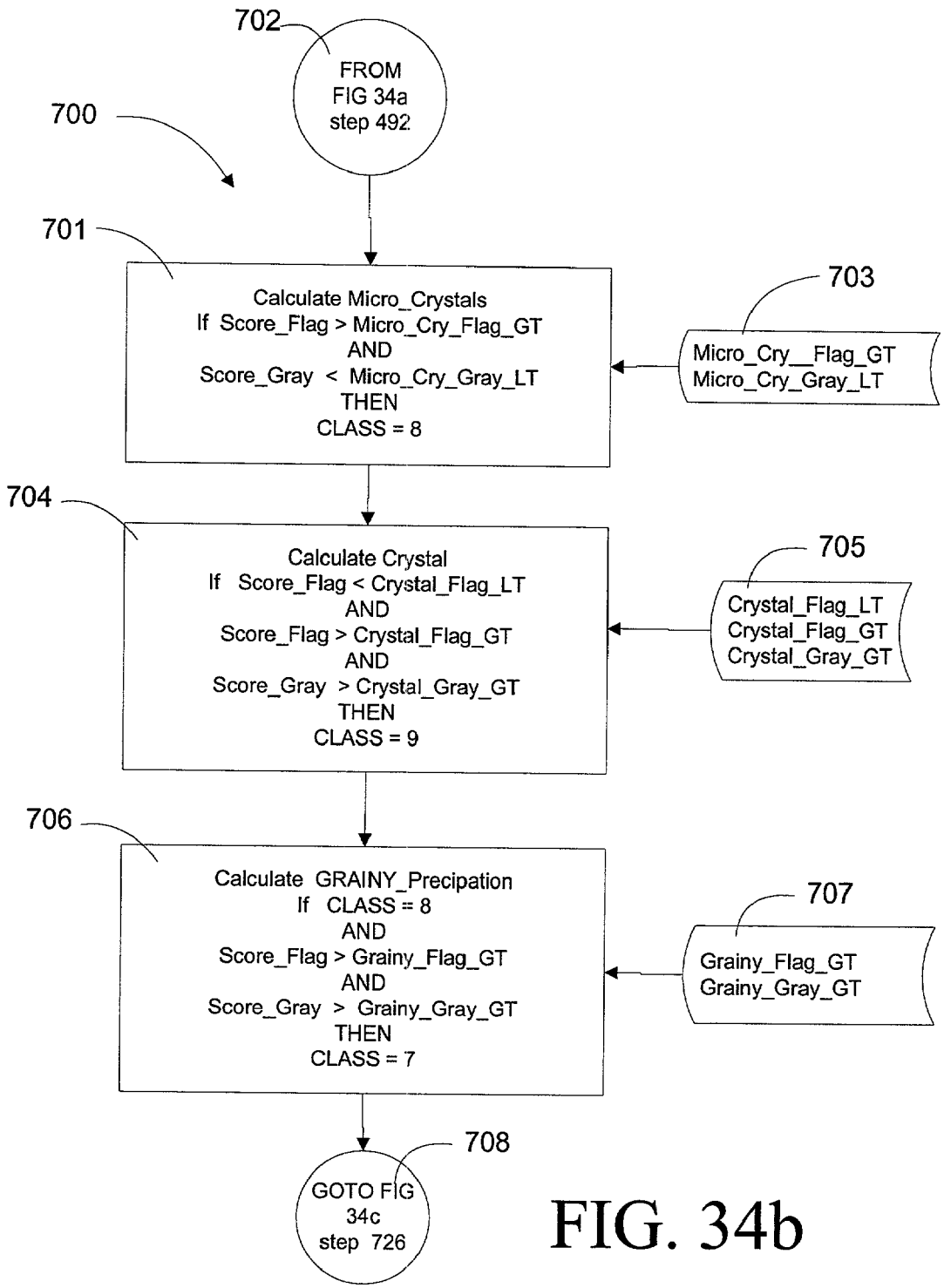

Step 492 continues the classification process in FIG. 34b.

In FIG. 34b, the continuation of the classification process 700 is shown continuing in step 702. Step 704 calculates micro_crystals by using thresholds detailed in step 703 (Micro_Cry_Flag_GT and Micro_Cry_Gray_LT) with the following equation: if score_flag is greater than Micro_Cry_Flag_GT and score_gray is less than Micro_Cry_Gray_LT, then set CLASS=8.

Step 704 calculates crystals by using thresholds detailed in step 705 (Crystal_Flag_LT, Crystal_Flag_GT, and Crystal_Gray_GT) with the following equation: if score_flag is less than Crystal_Flag_LT and score_flag is greater than Crystal_Flag_GT and score_gray is greater than Crystal_Gray_GT then set CLASS=9.

Step 706 calculates Grainy precipitation by using thresholds detailed in step 707 (Grainy_Flag_GT, and Grainy_Gray_GT) with the following equation: if CLASS=8 and score_flag is greater than Grainy_Flag_GT and score gray is greater than Grainy_Gray_GT, then set CLASS=7.

Figure 34C:
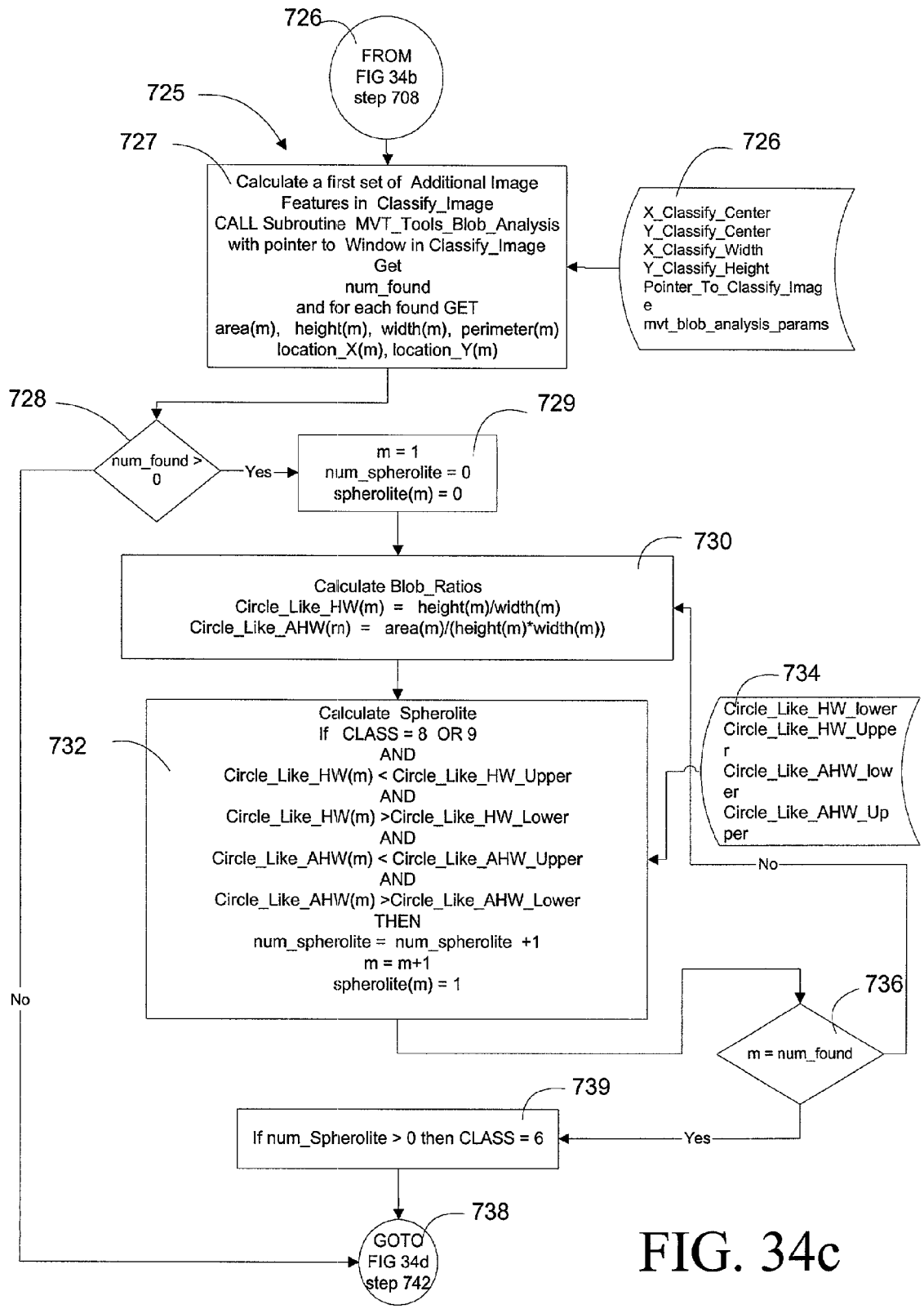

Step 708 continues the classification process onto FIG. 34c as 725.

Step 726 continues from step 708 of FIG. 34b.

In FIG. 34c, Step 727 calculates and generates a first set of additional image features for further use in classification taking as input 726 (X_Classify_Center, Y_Classify _Center, X_Classify_Width, Y_Classify Height, Pointer_to_classify_image, and mvt_blob_analysis Params). In step 727, MVT_Tools_Blob_Analysis with pointer to window in Classify_Image is called. Step 727 gets the num_found of blobs and, for each blob found, step 727 gets its area(m), height(m), width(m), perimeter(m), and location of each as location_X(m) ands location_Y(m). These values are recorded. These calculations are performed on the image called Classify_Image, which is the image that was formed in FIG. 33 as step 458.

In step 728, if num_found is not greater than zero(0) the subroutine goes to step 738. However, if any blobs are found then further analysis is started in step 729 by setting m=1, num_spherolite=0, and spherolite(m)=0. In step 730, the following blob_ratios are calculated: Circle_Like_HW(m) =height(m)/Width(m) and Circle_Like_AHW(m)= area(m)/(height(m)*width(m)). For blobs that are circular, Circle_Like_HW will be around a value of one (1). If blobs get elongated then the value will be other than one. Circle_Like_AHW for circular blobs has a value around 0.785. For square-like blobs the value will be closer to one (1). The program flow goes onto step 732.

Step 732 determines whether to classify a drop as having a spherolite by utilizing the parameters found in 734 (Circle_Like_HW_lower, Circle_Like_HW_Upper, Circle_Like_AHW_Lower, and Circle_Like_AHW_Upper). The following equation is used: if CLASS=8 or 9 and Circle_Like_HW(m) is less than Circle_Like_HW_Upper and Circle_Like_HW(m) is greater than Circle_Like_HW_lower, and Circle_Like_AHW(m) is less than Circle_Like_AHW_Upper and Circle_Like_AHW(m) is greater then Circle_Like_AHW_Lower, then num_spherolite=num_sperolite+1. An increment is done by calculating m=m+1 and setting spherolite(m)=1 to show one has been found at m.

Step 736 tests whether all of the found blobs have been classified by testing m against num_found and, if equal, the subroutine goes onto step 738. If not the program loops back to step 730 and flows through as above.

Figure 34D:
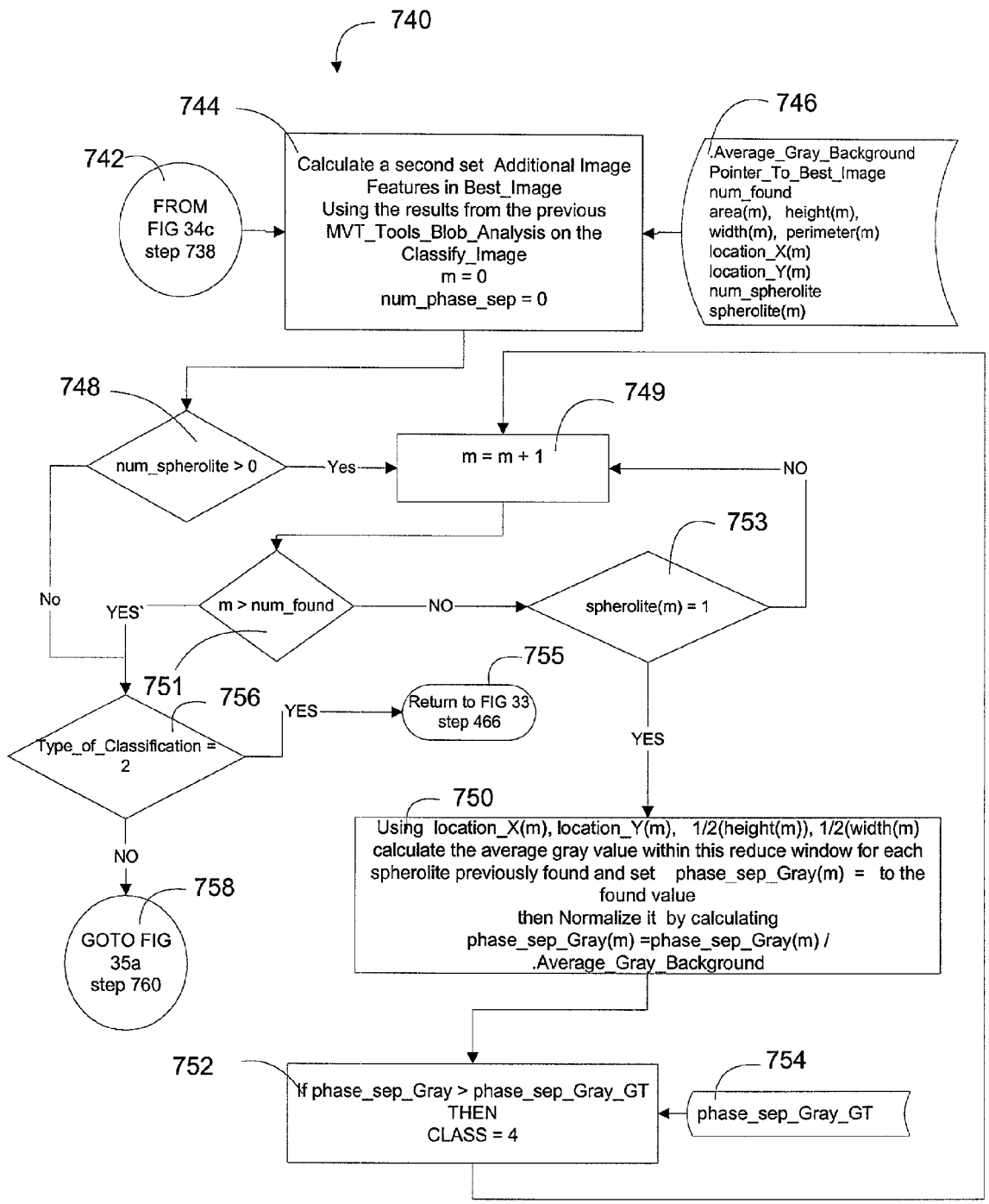

Step 738 goes onto FIG. 34d in the classification subroutine as 740.

FIG. 34d continues from FIG. 34c at 742 and goes to 744 where a second set of additional features is calculated. These features are generated with the original Best_Image generated in step 328 (FIG. 31) as the image of the best focus. For these additional features, the results are used from the blob analysis performed in FIG. 34c on the classify_image. Such features as shown in parameters 746 as num_found, area(m), height(m), width(m), perimeter(m), location_X(m), location_Y(m), num_spherolite, and spherolite(m). Plus it uses the average_gray background from FIG. 33 step 448, and the pointer_to_Best_Iimage in FIG. 31 step 328. In step 744 "m" and num_phase_sep are set equal to zero.

In step 748, if the number of spherolites previously found (num_spherolite) is not greater than zero (0), then the flow goes to step 756 and the remaining steps shown in FIG. 34d are bypassed. But if the num_spherolite is greater than zero (0), then the flow goes onto step 749 wherein m is incremented by 1. Then the flow goes on to step 751 to test whether to go to step 756 or to step 753 depending on comparing "m" to the num_found. In step 753, the value of spherolite(m) found in FIG. 34c step 732 is tested to see if any were classified as spherolite. If not, then the flow loops back to step 749. If spherolite(m) is equal to one (1) then step 750 is executed.

In step 750, the information location_X(m), location_Y(m), one half of height(m) and one half of width(m) is used to calculate the average gray value within this reduced image inside each spherolite. The Best_Image pixel data obtained from the previous blob analysis is utilized and phase_sep_Gray(m) is set equal to this value. Phase_sep_Gray(m) is then normalized by dividing it by the Average_Gray_Background. The program flow goes onto step 752, wherein phase_sep_Gray(m) is tested to see if it is greater than a parameter phase_sep_Gray_GT from parameter input step 754. If true, then CLASS is set equal to four(4) and the program loops up to step 749.

In step 751 the automatic program has classified the microdrop into one of the 10 primary classes, 0 through 9, detailed previously in Table 1. Then, a test is made to see if the type _of_classification is equal to 2. If so, then the flow goes onto step 755 wherein the flow is returned to FIG. 33. In step 466, a general classification is complete. If further classification into subcategories is required, then the flow goes onto step 758.

Figure 35A:
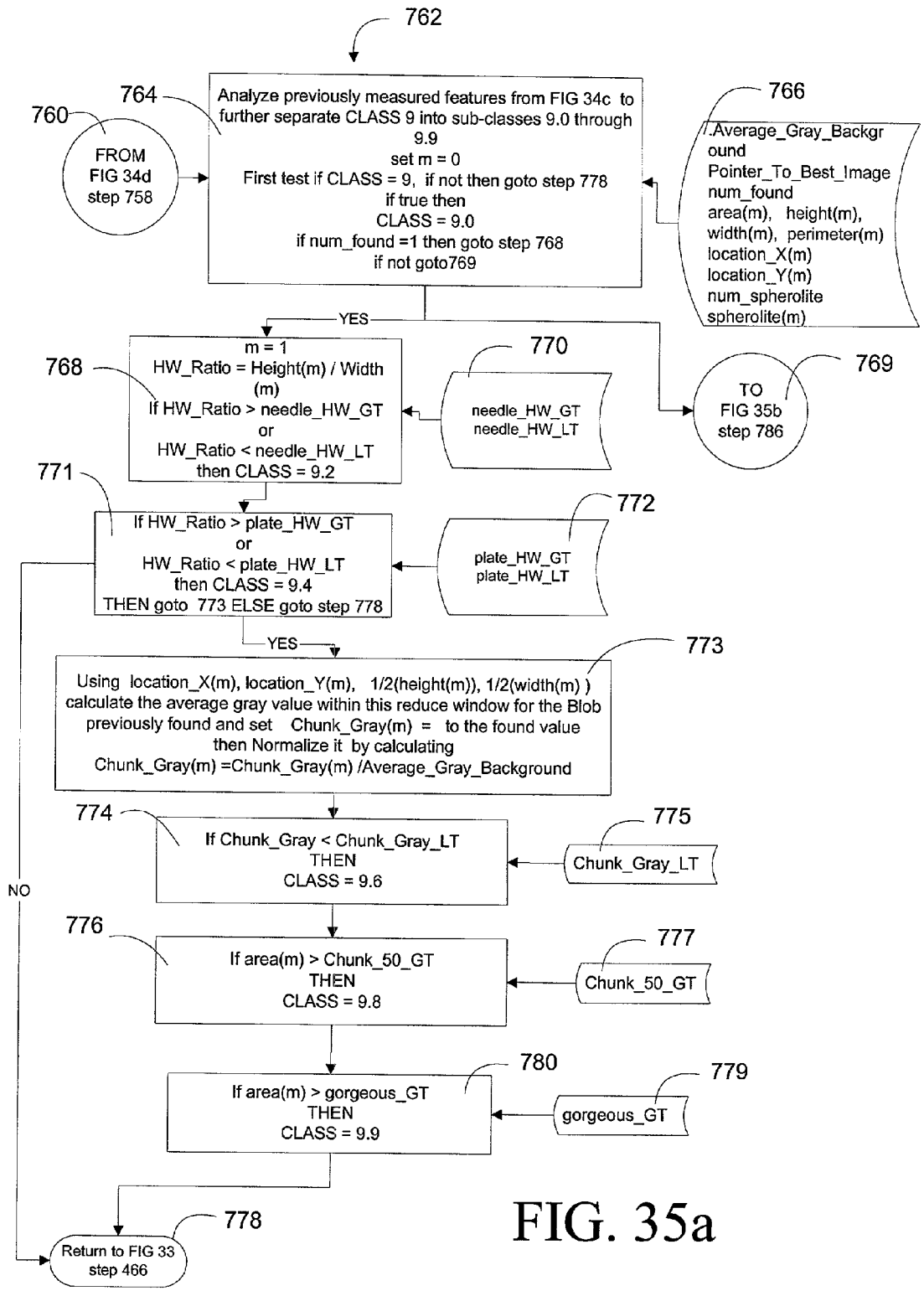
FIGS. 35a–35b show the sub-classification of the crystal class.

In step 758, the program flow goes onto FIG. 35a step 760.

In FIG. 35a, a crystal classification subroutine 762 further classifies any CLASS 9 crystal image into to additional subclasses, 9.2, 9.4, 9.6, 9.8, or 9.9, as previously discussed in Table 2. The subroutine begins at step 760 and goes onto step 764. In step 764, the blob counter m is set to zero. A test is conducted to see if the CLASS is equal to 9 and, if not, the flow goes to step 778 and returns to FIG. 33 step 466. Step 764 uses input values as shown in step 766 (Average_Gray_Background, Pointer_To_Best_Image, num_found, area(m), height(m), width(m), perimeter(m), location_X(m), location_Y(m), num_spherolite, and spherolite(m)), as previously described. If the CLASS is equal to 9 another test is made to see if one or more than one blobs were previously found. If only one blob was previously found then the flow goes onto step 768. If more then one is found, the flow goes onto step 769 in FIG. 35b. In step 768, a height to width ratio is calculated and compared to thresholds representing needle-like characteristics in step 770. If the test conditions are met, then the CLASS is set to 9.2. If not, the flow goes onto step 771. In step 771, the height to width ratio is compared to thresholds representing plate-like characteristics in step 772. If the conditions of the test are met, the CLASS is changed to 9.4 and the flow goes onto step 773. If not, no further classification is performed and the flow goes onto step 778 and the subroutine returns to FIG. 33 step 466. In step 773, a normalized average gray value, Chunk_Gray(m), within the blob is calculated and the flow goes onto step 774. In step 774, if Chunk_gray(m) is less than a threshold Chunck_Gray_LT (from step 775), then CLASS is set to 9.6 and the flow goes onto step 776. In step 776, if Chunk_gray(m) is greater than a threshold Chunk_50_GT, (from step 777), then CLASS is set to 9.8 and the flow goes onto step 780. In step 780 if area(m) is greater than threshold gorgeous_GT (from step 779), then CLASS=9.9 and the flow goes onto step 778. Then the subroutine returns to FIG. 33 step 466.

Figure 35B:
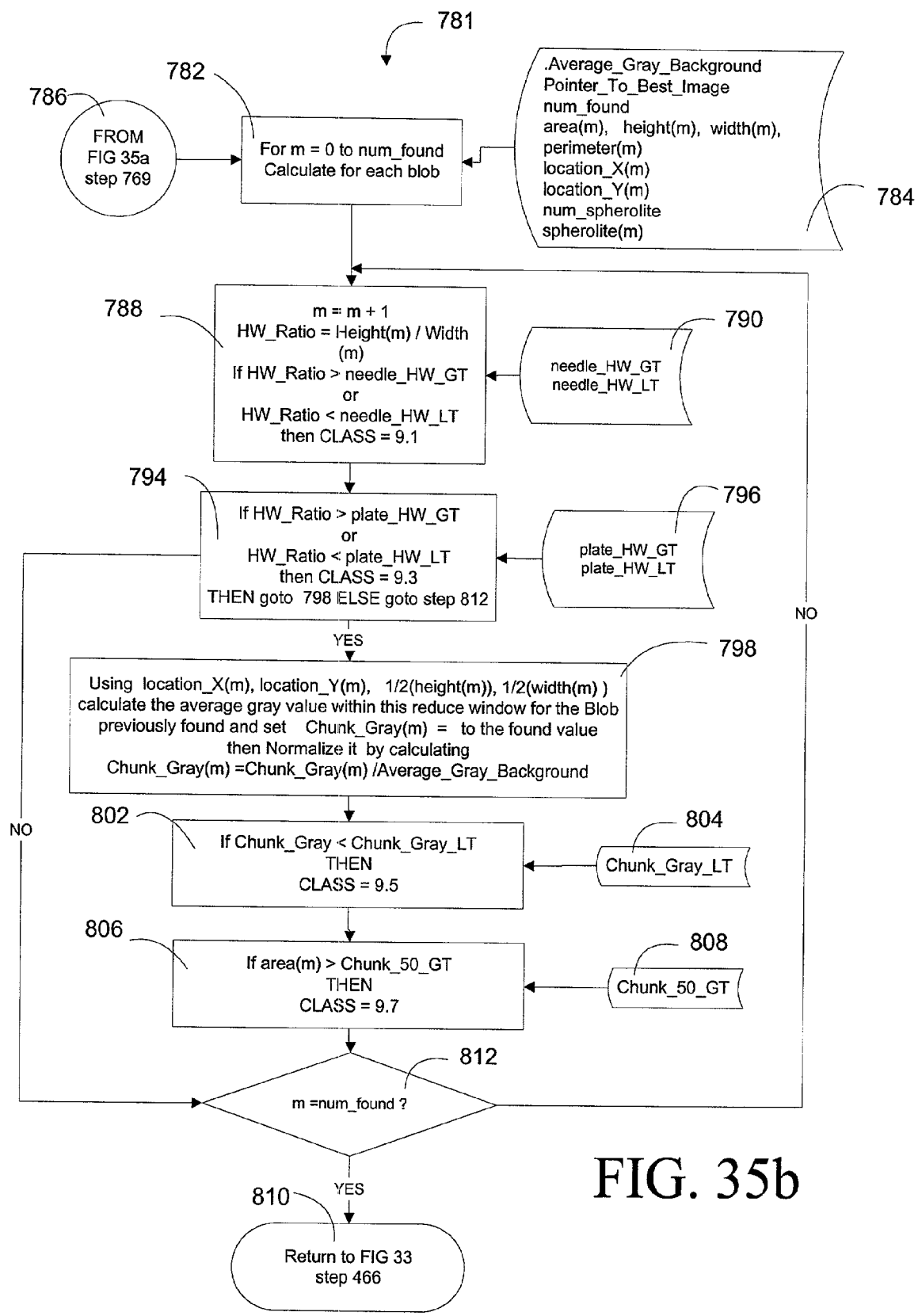

FIG. 35b shows flowchart 781 illustrating the further classification of a CLASS 9 image having multiple blobs within the image into additional subclasses, 9.1, 9.3, 9.5, or 9.7, as previously discussed in Table 2. The subroutine begins at step 786 from step 769 in FIG. 35a and goes onto step 782. In step 782, a loop begins at m equals 0 for each blob m using input values from step 784 (Average_Gray_Background, Pointer_To_Best_Image, num_found, area(m), height(m), width(m), perimeter(m), location_X(m), location_Y(m), num_spherolite, and spherolite(m)) as previously described. The flow goes onto step 788 where m is incremented and a height to width ratio is calculated and compared to thresholds representing needle-like characteristics in step 790. If the test conditions are met, then the CLASS is set to 9.1. If not, the flow goes onto step 794. In step 794, the height to width ratio is compared to thresholds representing plate-like characteristics in step 796. If the conditions of the test are met, the CLASS is changed to 9.3. If not, no further classification is performed and the flow goes onto step 812 to determine if all of the blobs have been tested. In step 798, a normalized average gray value (Chunk_Gray(m) as described before) within the blob is calculated and the flow goes onto step 802. In step 802, if Chunk_gray(m) is less than a threshold Chunk_Gray_LT (from step 804) then CLASS is set to 9.5 and the flow goes onto step 806. In step 806, if Chunk_gray(m) is greater than a threshold Chunk_50_GT (from step 808) then CLASS is set to 9.7 and the flow goes onto step 812. In step 812, if all of the blobs have been tested, the flow goes onto step 810 and the subroutine returns to FIG. 33 step 466. If not all tested, then the flow loops back to step 788 for the next blob and the process loops until complete.

Typical parameter and threshold values for use in classification in FIGS. 33, 34a, 34b, 34c, 34d, and 35a and 35b are given in Table 3 along with the preferred value. These values serve only as a guide, and other values may be used when circumstances justify. For example, different lighting conditions, variations in the transparency of micro-well plates, variations in the formulations of the protein growing media and drop, values may be used as well. One skilled in the art may adjust the parameter and threshold values to tune in the classification results specific to their setup.

TABLE 3

Typical and preferred values for threshold and Classification parameters

| Step | Name | lower value | upper value | Preferred value |
|---|---|---|---|---|
| 452 | Diff_Sep | 1 | 20 | 7 |
| 452 | Set1 | 1 | 511 | 128 |
| 452 | Set2 | 1 | 511 | 200 |
| 452 | Flag_Thresh | 5 | 50 | 25 |
| 478 | Lgt_Precip_Flag_LT | 0.0001 | 0.010 | 0.002 |
| 478 | Lgt_Precip_Flag_GT | 0.0 | 0.001 | 0.00001 |
| 478 | Lgt_Precip_Gray_GT | 0.8 | 1.2 | 1.020 |
| 482 | Clear_Flag_LT | 0.000001 | 0.01 | 0.0007 |
| 482 | Clear_Gray_GT | 0.8 | 1.2 | 1.020 |
| 486 | Heavy_Precip_Flag_LT | 0.0001 | 0.050 | 0.020 |
| 486 | Heavy_Precip_Flag_GT | 0.0 | 0.005 | 0.001 |
| 486 | Heavy_Precip_Gray_LT | 0.7 | 1.2 | 0.95 |
| 490 | Ugly_Precip_Flag_LT | 0.0001 | 0.050 | 0.020 |
| 490 | Ugly_Precip_Flag_GT | 0.0 | 0.005 | 0.001 |
| 490 | Ugly_Precip_Gray_LT | 0.5 | 1.2 | 0.7 |

TABLE 3-continued

Typical and preferred values for threshold and Classification parameters

| Step | Name | lower value | upper value | Preferred value |
|---|---|---|---|---|
| 703 | Micro_Cry_Flag_GT | 0.0001 | 0.05 | 0.020 |
| 703 | Micro_Cry_Gray_LT | 0.9 | 1.20 | 1.010 |
| 705 | Crystal_flag_LT | 0.1 | 0.5 | 0.30 |
| 705 | Crystal_Flag_GT | 0.001 | 0.05 | 0.01 |
| 705 | Crystal_Gray_GT | 0.8 | 1.2 | 1.0099 |
| 707 | Grainy_Flag_GT | .001 | .5 | 0.177 |
| 707 | Grainy_Gray_GT | 0.8 | 1.2 | 0.980 |
| 734 | Circle_Like_HW_lower | 0.5 | 1.00 | 0.9 |
| 734 | Circle_Like_HW_Upper | 1.00 | 2.0 | 1.1 |
| 734 | Circle_Like_AHW_lower | 0.1 | 3.9 | 0.78 |
| 734 | Circle_Like_AHW_Upper | .785 | 2.0 | 0.83 |
| 754 | phase_sep_Gray_GT | 0.9 | 1.2 | 1.05 |
| 770, 790 | needle_HW_GT | 2 | 20 | 5 |
| 770, 790 | needle_HW_LT | 0.5 | 0.05 | 0.2 |
| 772, 796 | plate_HW_GT | 1.1 | 2.0 | 0.95 |
| 772, 796 | plate_HW_LT | 0.9 | 1.1 | 1.05 |
| 775, 804 | Chunk_Gray_LT | 0.8 | 1.2 | 1.01 |
| 777, 808 | Chunk_50_GT | 70 | 200 | 100 |
| 779 | Gorgeous_GT | 7000 | 2000 | 1000 |

Prototype

Applicants have designed, built and tested a working prototype of the present invention.

Figure 30:
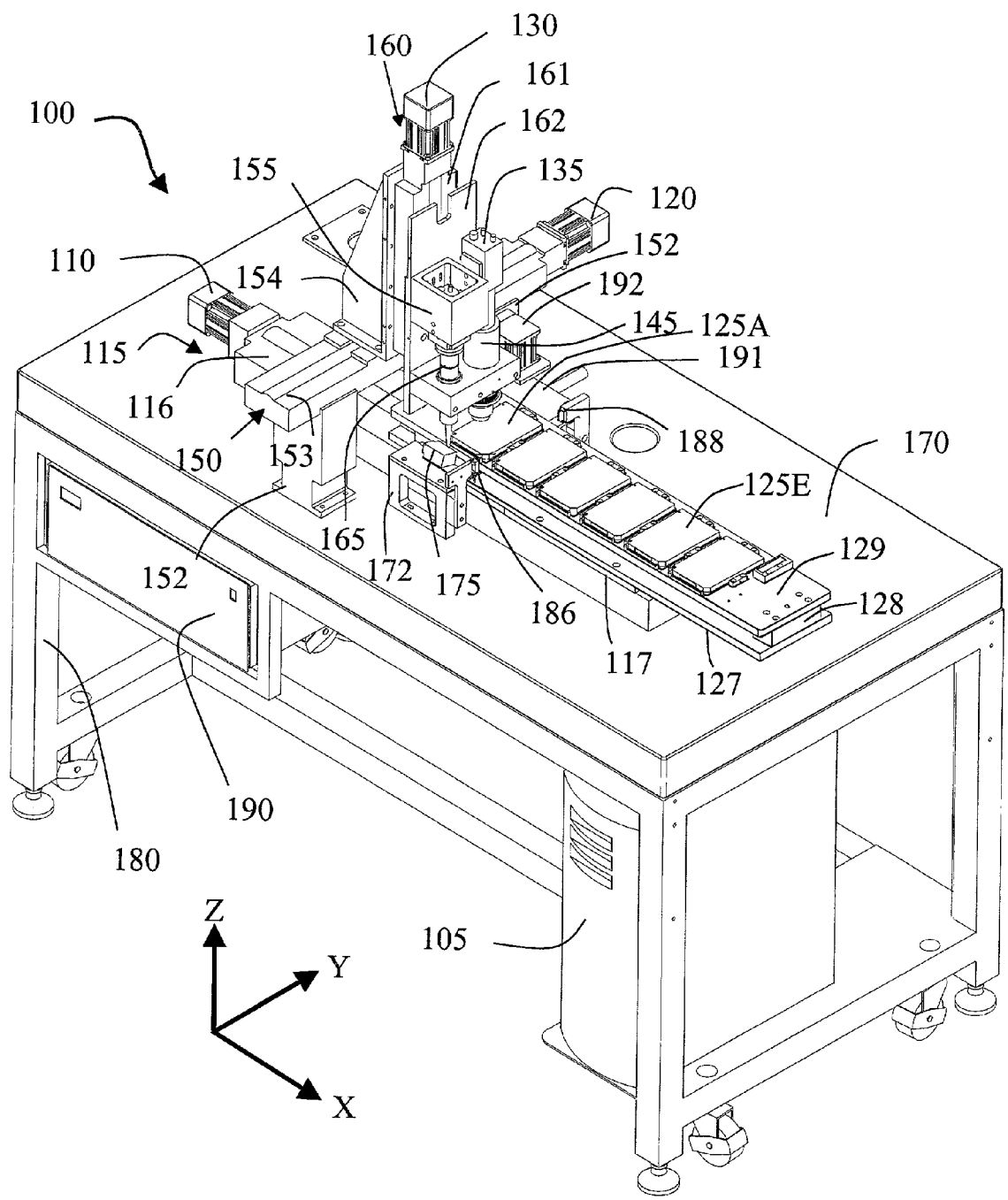
FIG. 30 shows a preferred embodiment of the present invention.

FIG. 30 shows the major components of the Applicant's prototype. Proteomic crystal verification and inspection system 100 has three axis of linear motion. Linear actuator 115 is preferably linear actuator model # 802-0763D available from Dynamic Solutions of Irvine Calif., with 600 mm of travel driven by an enclosed 0.5 mm pitch ballscrew. Linear actuator 115 is driven by an intelligent self-contained servo motor 110 model # SM2320 SQ available from Animatics Corp. of Santa Clara, Calif., with 38 oz-in of available torque. Servo motor 110 communicates with a Windows Based computer 105 through a serial connection routed through a central control unit 190.

Linear actuator 115 has stationary part 116 fixed to a granite table top 170. Motor 110 moves moving part 117 along the x-axis. Granite top 170 is supported by a frame 180. Frame 180 has casters and adjustable legs. Plate 127 is attached to moving part 117. At each end of plate 127, a spacing block 128 spaces fixture plate 129 from plate 127. At each of its ends, fixture plate 129 is supported by spacing block 128. Fixture plate 129 provides for the mounting, removal, and positioning of multiple micro-well plates 125A–125F. Preferably micro-well plates 125A–125F are agar plates, micro-titer well plates of 96, 384, 1536 wells, or other sample plates.

Support 191 is positioned adjacent to fixture plate 129 and contains a light source. In the preferred embodiment, the light source is model # A08925 fiber-optic back light available from Aegis Electronics of Carlsbad, Calif.

In the preferred embodiment, linear actuator 150 is model # 802-1384A available from Dynamic Solutions of Irvine Calif., with 350 mm of travel driven by an enclosed 0.5 mm pitch ballscrew. Linear actuator 150 has stationary part 153 horizontally bridged above linear actuator 115 and supported by pillars 152. Moving base 154 provides a mounting base for components of linear actuator 160. In a preferred embodiment, linear actuator 150 is driven by driven by an intelligent self-contained servo motor 120 identical to motor 110. Servo motor 120 communicates with Windows Based computer 105 through a serial connection routed through central control unit 190.

In a preferred embodiment, linear actuator 160 is model # 802-0756D available from Dynamic Solutions of Irvine Calif., with 100 mm of travel driven by an enclosed 0.5 mm pitch ballscrew. Linear actuator 160 has with a stationary part 161 mounted perpendicular to and fixed to moving base 154 of linear actuator 150. Linear actuator 160 is driven by intelligent self-contained servo motor 130. Servo motor 130 is preferably identical to motor 110. Servo motor 130 communicates with the Windows Based computer 105 through a serial connection routed through the central control unit 190.

Moving plate 162 provides a mounting base for camera 155. In a preferred embodiment camera 155 is a high-resolution monochrome megapixel CCD camera model # CVM1 from JAI America INC. of Laguna Hills, Calif. Camera 155 has lens 165. Preferably, lens 165 has a 0.75× to 3× zoom capability and is model # NT52-571 available from Edmund Industrial Optical of Barrington, N.J. Moving plate 162 also provides a mounting base for camera 135. Preferably, camera 135 is a high-resolution monochrome megapixel CCD camera model # CVM1 from JAI America INC. of Laguna Hills, Calif. Camera 135 has lens 145. Preferably, lens 145 has a 2.5× to 10× zoom capability and is model # NT54-396 available from Edmund Industrial Optical of Barrington, N.J.

Moving plate 162 also provides a mounting base for a zoom lens motor 192, an intelligent self-contained servo motor model # SM2315D available from Animatics Corp. of Santa Clara, Calif., with 20 oz-in of available torque. The servo motor communicates with the Windows Based computer 105 through a serial connection routed through the motion control box 190. The zoom lens motor operates the zoom lens 145 through a conventional belt drive.

A bar-code reader 175 is mounted adjacent linear actuator 115 and is attached to support 172 fixed on granite top 170. Bar-code reader 175 is positioned to view a bar-code identity label attached to a micro-well plate when the micro-well plate is positioned under linear actuator 150. Preferably, bar-code reader 175 is model # BL601 available from Keyence Corporation of America of Newark, N.J.

A plate sensor transmitter/receiver 186 is also fixed to support 172 and is aligned to sense whenever a micro-well plate 125 breaks a beam of light emitted by transmitter/receiver 186 and reflected by a reflector 188. Reflector 188 is mounted on support 191 on the opposite side of the linear actuator 115. Plate sensor transmitter/receiver 186 and reflector 188 are preferably model # E3T-SR13 available from Western Switch Controls of Santa Ana, Calif.

Block Diagram Showing Connectivity of the Prototype

Figure 6:
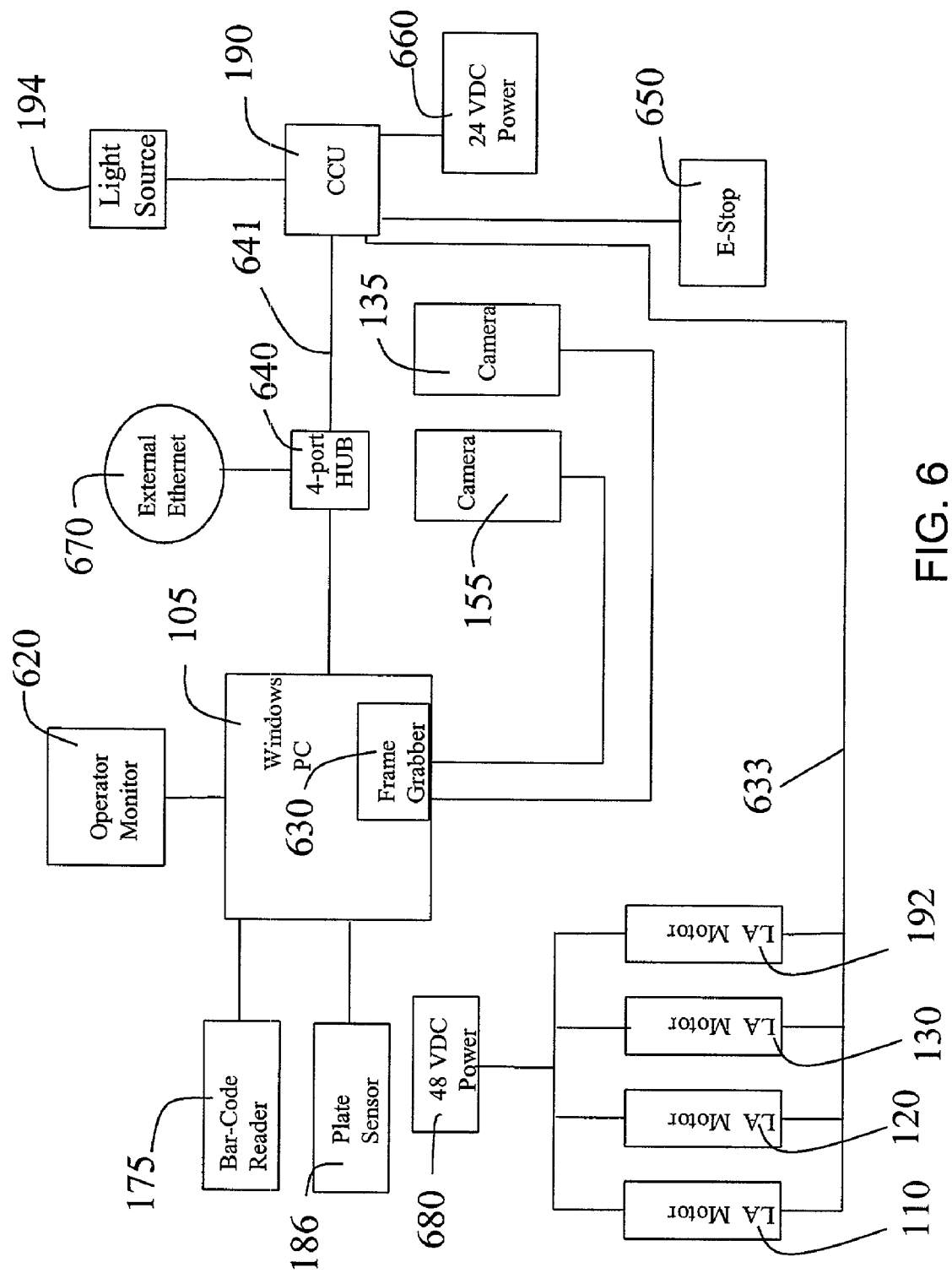
FIG. 6 shows a block diagram of a preferred embodiment of the present invention.

FIG. 6 shows a block diagram illustrating the connectivity of Applicant's prototype. Linear actuator motors 110, 120 and 130, and zoom motor 192 receive DC power from 48 Volt DC power supply 680 through an electrical connection. Linear actuator motors 110, 120 and 130, and zoom motor 192 motors communicate with Windows-based computer 105 through common serial line 633. Bar-code reader 175 communicates with computer 105 through a communications line and plate sensor 186 communicates with the computer 105 through a communications line. Monitor 620 displays information to the operator transmitted from computer 105. Cameras 135 and 155 communicate with frame grabber 630 through communication lines. Frame grabber 630 is installed within computer 105 and is preferably PCVision from Coreco Imaging US Office in Bedford, Mass. Frame grabber 630 digitizes the image from the camera to form the digitized image data array within computer 105. A 4-port Ethernet hub 640 provides for connectivity between computer 105, central control unit 190, and an external Ethernet 670. By providing for connectivity to the Ethernet, computer network communications are possible. The central control unit 190 controls light source 194 through an analog control line. Central control unit 190 receives 24 volt DC power from 24 volt DC power supply 660. Emergency stop button and switch (e-stop) 650 is connected to central control unit 190.

Experimental Results

Fifty-three test images were obtained from the system and were both automatically classified by the system and were manually classified by four scientists. Table 4 shows the correlation percentage between the various scientists and the automatic classification provided by the system.

TABLE 4

|       | Sam  | Mary | Susan | Fred | AUTO |
|-------|------|------|-------|------|------|
| Sam   | 100% |      |       |      |      |
| Mary  | 98%  | 100% |       |      |      |
| Susan | 93%  | 97%  | 100%  |      |      |
| Fred  | 89%  | 93%  | 96%   | 100% |      |
| AUTO  | 95%  | 93%  | 86%   | 81%  | 100% |

Utilization of Color

In another preferred embodiment, the present invention is configured to record color images. It is desirable to be able to analyze color images in that certain precipitation products in the protein crystallization process have distinctive colors and a crystallographer or automated image analysis algorithm may use the color information to help discriminate crystallization results.

True Color Picture

Figure 37:
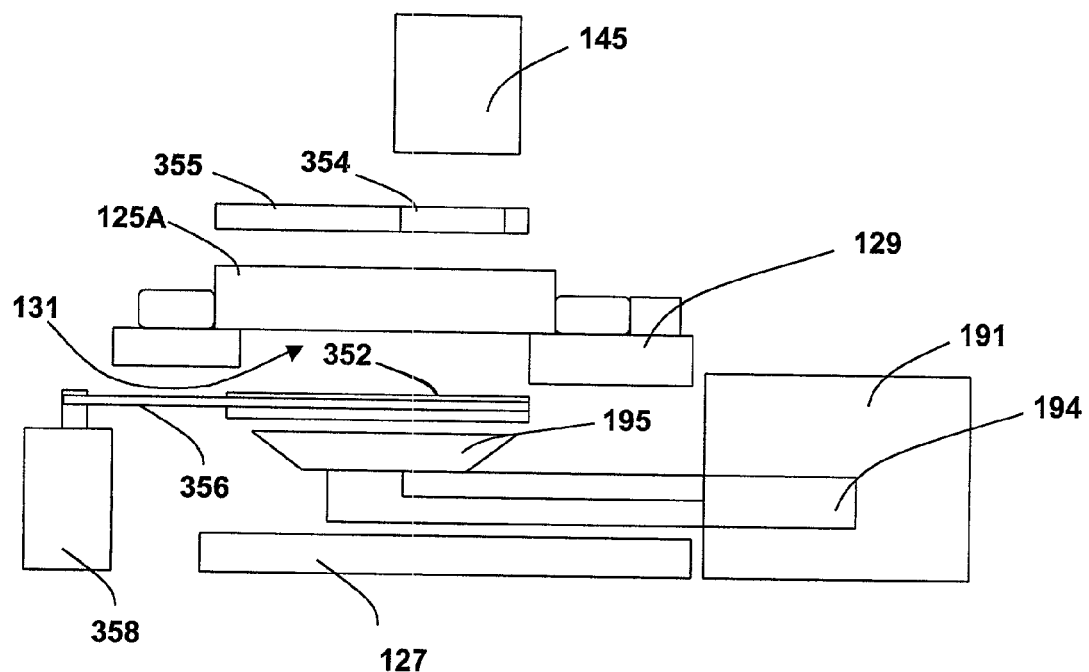
FIG. 37 illustrates a side view illustrating dual filters in the light path.

FIG. 37 shows a side view of micro-well plate 125A positioned on fixture plate 129. Support 191 with embedded light source 194 is positioned to the side of fixture plate 129. Light from light guide 195 is directed upward through cutout 131. Light guide 195 is positioned between fixture plate 129 and plate 127 such that both plates can move around the light guide 195 without interference.

Figure 38:
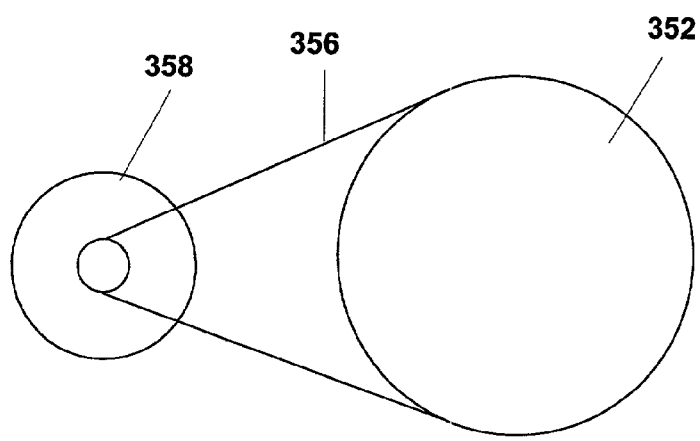
FIG. 38 illustrates a top view of the drive mechanism for the rotatable linear polarized filter.
Figure 39:
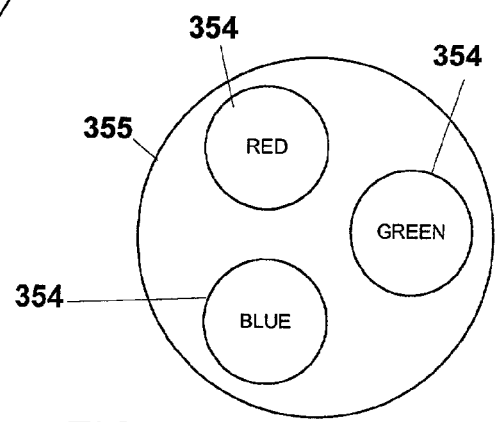
FIG. 39 illustrates a top view of a second filter wheel.
Figure 40:
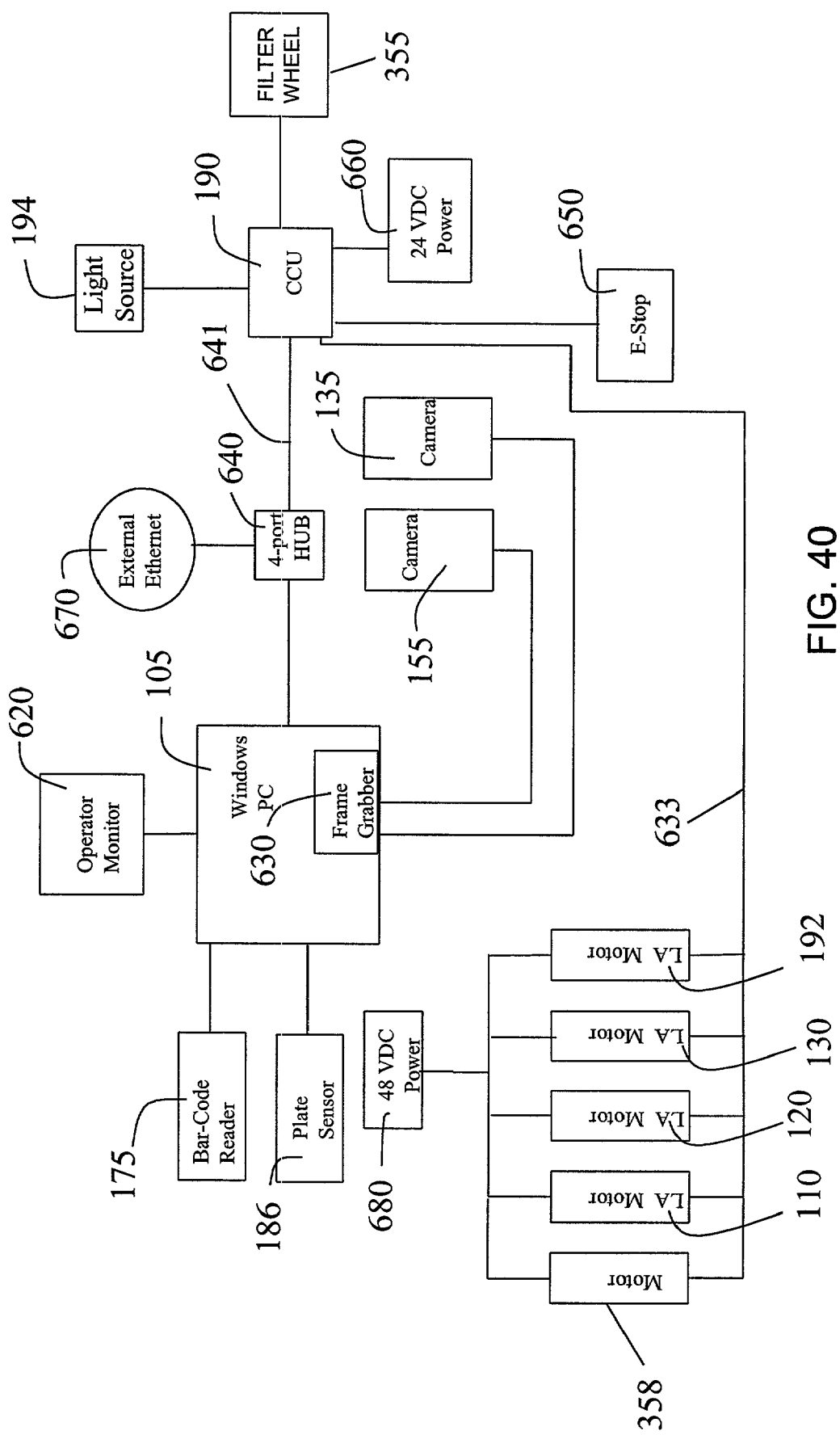
FIG. 40 shows the connectivity of another preferred embodiment.

Linear polarized filter 352 is rotationally mounted above light guide 195 such that light from light guide 195 can be polarized linearly at a programmable angle before it transits through micro-well plate 125A. Polarizer drive belt 356 (top view shown in FIG. 38) rotates polarized filter 352 about a vertical axis. Polarization drive belt 356 is driven by motor 358. Motor 358 is controlled by CCU 190 (FIG. 40). Second filter 354 (top view shown in FIG. 39) is positioned above micro-well plate 125A such that light transiting through micro-well plate 125A goes through second filter 354 before it goes into the camera zoom lens 145. Second filters 354 are mounted on filter wheel apparatus 355. Filter wheel apparatus 355 rotates the operator selected second filter 354 into position under the zoom lens 145. The selected second filter 354 is preferably either a red, green or blue dichroic filter. Preferably, individual images taken through the red, green and blue second filters are combined to form a true color image.

False Color Image

In addition to the true color images that may be formed using red, green, and blue filters 354, a false color (also called a pseudo color) image may be formed by taking three individual images using linear polarized filter 352 at three different polarization angles with respect to a second filter. In this preferred embodiment, a linear polarized filter is substituted for the dichroic second filters 354 discussed above. For example, the polarized axis may be at 90 degrees to each other, and at plus and minus 45 degrees to each other. The three images are then called red, green, and blue and a false color image is produced. If the crystal exhibits any polarization rotation effects, then a very colorful image results. This pseudo color image is useful in detecting very small and fine crystals from the image background material. Other polarizing angles may be selected as well.

In the preferred embodiment, light guide 195 is model # A08925 fiber-optic backlight available from Aegis Electronics of Carlsbad. Calif. Light source 194 is a Dolan-Jenner Model-PL-900 available from Edmund Industrial Optics, Barrington, N.J. First polarized filter 352, second filter 354 (including the linear polarized filters, and the dichroic red, green, blue filters) are available from Edmund Industrial Optics, Barrington, N.J. Filter wheel 355 is model FW1 available from Integrated Scientific Imaging Systems, Inc of Santa Barbara, Calif.

Figure 12:
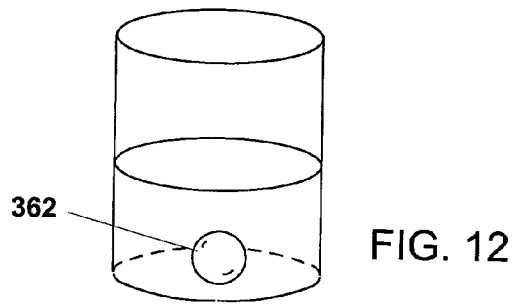
FIG. 12 shows an example of aqueous drop in oil protein crystallization.

Although the above-preferred embodiments have been described with specificity, persons skilled in this art will recognize that many changes to the specific embodiments disclosed above could be made without departing from the spirit of the invention. For example, although the above preferred embodiments specifically describe an indexing device in which linear actuators 115, 150, and 160 operate in conjunction to sequentially position protein crystals under cameras 155 and 135, there are a variety of other types of robotic indexing devices that could also be utilized for the same purpose. For example, an indexing device could be built in which the plurality of micro-well plates are kept in a stationary position. The camera lens would be attached to an indexing device that is preferably capable of unrestricted movement in the horizontal plane. The camera lens would be moved sequentially from micro-well to micro-well in the horizontal plane. Once in position over a micro-well, the lens could be raised or lowered in the vertical direction to achieve proper zoom and focus. In another embodiment, an indexing device could be built in which cameras 155 and 135 are kept stationary with respect to horizontal movement. In this embodiment, the plurality of micro-well plates would be preferably placed on a positioning platform that is capable of unrestricted movement in the horizontal plane. In this fashion, the positioning platform could be moved so that each micro-well is sequentially positioned underneath the appropriate camera. As with the previous embodiment, once in position over a micro-well, the lens could be raised or lowered in the vertical direction to achieve proper zoom and focus. Also, although the first preferred embodiment discussed inspecting crystals grown by the hanging drop method, other crystals grown utilizing other methods could be inspected with equal effectiveness. For example, FIG. 12 shows protein crystal growth as a result of aqueous drop in oil protein crystallization. Cameras 135 and 155 focus on the crystals in drop 362. Also, although the above preferred embodiments discussed in detail how the present invention is utilized for inspecting protein crystals inside drops of liquid, the present invention could also be utilized to inspect other types of microscopic specimens. For example, the present invention could be utilized to inspect typical micro-well micro titer plate reactions wherein the quality of the reaction can be judged by the amount and wavelength of fluorescence emitted by the specimen by configuring the system with appropriate light sources, filters, and sensitive cameras as is typical for fluorescence detection. Also, although the above preferred embodiments disclosed the utilization of two cameras 135 and 155, it would also be possible to have just one camera that is capable of zooming out so that it can focus on the entire well and zooming in so that it can focus on the drop of liquid containing the crystal. In addition, although an area CCD camera is shown, a linear CCD camera combined with moving of the micro-well plate would also work in the present invention. Also, in another preferred embodiment the detents 510 and 520 can be simply spring loaded and not controlled by the computer 105. Also, the invention is taught with a light panel light source, and or a bulb, likewise LED light sources and laser light sources could also be used with the present invention. Although the system is shown that only moves the micro-well plates in one axis and the camera in the other two axes, the invention could likewise be practiced with either the micro-wells moving in two orthogonal axes (such as X and Y) while the camera moves only in the Z-axis or the motion of all three axes be done with the camera system, wherein the micro-well plates are stationary and the system moves above them. These other variations of system design could also require rearrangement of the light source or multiple light sources. Also, other filter types may be substituted for second filter 354. For example, a linearly polarized filter would be very effective. Also, although the above preferred embodiments disclosed specific types of cameras 135 and 155, other CCD cameras may be used in the present invention with less resolution or with greater resolution and still practice the present invention. For example, cameras of 2,000 by 2,000 pixels and even 4,000 by 4000 pixels are commercially available from several vendors. When digitizing these alternative cameras, the digitized image would have the corresponding resolution of the camera. Also, one may practice this invention and digitize to greater gray-scale accuracy than 8-bit and gain advantage if the camera supports the greater bit depth, for example if the camera were cooled to reduce image noise. Therefore, the attached claims and their legal equivalents should determine the scope of the invention.

We claim:

1. A device for inspecting and classifying a plurality of microscopic crystals, comprising:

A) at least one camera,
B) an indexing device for sequentially placing said microscopic crystals in camera-view of said at least one camera, and
C) at least one computer programmed to control said indexing device and said at least one camera, wherein said at least one computer is programmed to receive from said at least one camera images of said plurality of microscopic crystals, wherein said at least one computer is programmed to classify said plurality of microscopic crystals by:
1. comparing said images to a database stored on said at least one computer, and
2. assigning a classification based on said comparison by:
a. automatically making a first determination if said image is clear, and
b. automatically making a second determination if said image is not clear, wherein said second determination is automatically chosen from a plurality of options, wherein said plurality of options comprises:
1. at least one option corresponding to what is present if said microscopic crystal does not exist, and
2. at least one option corresponding to what is present if said microscopic crystal does exist.

2. The device for inspecting and classifying a plurality of microscopic crystals as in claim 1, further comprising a computer monitor, wherein an operator interfacing with said at least one computer manually inputs a score to classify said plurality of microscopic crystals after observing said plurality of microscopic crystals on said computer monitor.

3. The device for inspecting and classifying a plurality of microscopic crystals as in claim 1, wherein said at least one computer automatically classifies said plurality of microscopic crystals after receiving said images.

4. The device for inspecting and classifying a plurality of microscopic crystals as in claim 1, wherein said at least one camera is a first camera and a second camera, wherein said first camera is set at a constant zoom to cover a large field of view, wherein said second camera comprises a motorized zoom lens controllable by said at least one computer.

5. The device for inspecting and classifying a plurality of microscopic crystals as in claim 1, wherein each of said plurality of microscopic crystals are contained within a drop of liquid, wherein each drop of liquid is contained within a well of a micro-well plate.

6. The device for inspecting and classifying a plurality of microscopic crystals as in claim 1, wherein said plurality of microscopic crystals are a plurality of protein crystals inside the wells of at least one micro-well plate.

7. The device for inspecting and classifying a plurality of microscopic crystals as in claim 1, wherein said indexing device comprises:

A. a first linear actuator for horizontally positioning said positioning station,
B. a second linear actuator for horizontally positioning said at least one camera, and
C. a third linear actuator for vertically positioning said at least one camera.

8. The device for inspecting and classifying a plurality of microscopic crystals as in claim 7, wherein said at least one camera is a first camera and a second camera, wherein said first camera is set at a constant zoom to cover a large field of view, wherein said second camera comprises a motorized zoom lens controllable by said at least one computer.

9. The device for inspecting and classifying a plurality of microscopic crystals as in claim 1, further comprising a bar-code reader and a micro-well plate sensing device.

10. The device for inspecting and classifying a plurality of microscopic crystals as in claim 1, wherein said at least one computer comprises a frame grabber for receiving images of said plurality of microscopic crystals from said at least one camera.

11. The device for inspecting and classifying a plurality of microscopic crystals as in claim 1, wherein said at least one computer is connected to a computer network.

12. The device for inspecting and classifying a plurality of microscopic crystals as in claim 11, wherein said at least one computer network is the Ethernet.

13. A method for inspecting and classifying a plurality of microscopic crystals, comprising the steps of:
   A) sequentially placing said plurality of microscopic crystals in camera-view of at least one camera utilizing all indexing device,
   B) taking the images of said plurality of microscopic crystals with said at least one camera,
   C) transferring said images to at least one computer,
   D) receiving said images at said at least one computer, and
   E) classifying said images at said at least one computer, by comparing said images to a database stored on said at least one computer, and
   F) assigning a classification based on said comparison by:
      1. automatically making a first determination if said image is clear, and
      2. automatically making a second determination if said image is not clear, wherein said second determination is automatically chosen from a plurality of options, wherein said plurality of options comprises:
         a. at least one option corresponding to what is present if said microscopic crystal does exist, and
         b. at least one option corresponding to what is present if said microscopic crystal does exist.
wherein said at least one computer is programmed to automatically assign said classification, to control said at least one indexing device and said at least one camera.

14. The method for inspecting and classifying a plurality of microscopic crystals as in claim 13, wherein said step of classifying said images at said at least one computer is done manually, wherein an operator interfacing with said at least one computer and viewing a computer monitor manually inputs into said at least one computer a score to classify said plurality of microscopic crystals after observing said plurality of microscopic crystals on said computer monitor.

15. The method for inspecting and classifying a plurality of microscopic crystals as in claim 13, wherein said step of classifying said images at said at least one computer is done automatically at said at least one computer after receiving said images at said at least one computer.

16. The method for inspecting and classifying a plurality of microscopic crystals as in claim 13, wherein said at least one camera is a first camera and a second camera, wherein said first camera is set at a constant zoom to cover a large field of view, wherein said second camera comprises a motorized zoom lens controllable by said at least one computer.

17. The method for inspecting and classifying a plurality of microscopic crystals as in claim 13, wherein each of said plurality of microscopic crystals are contained within a drop of liquid, wherein said each drop of liquid is contained within a well of a micro-well plate.

18. The method for inspecting and classifying a plurality of microscopic crystals as in claim 13, wherein said plurality of microscopic crystals are a plurality of protein crystals inside the wells of at least one micro-well plate.

19. The method for inspecting and classifying a plurality of microscopic crystals as in claim 13, wherein said indexing device comprises:
   A. a first linear actuator for horizontally positioning said positioning station,
   B. a second linear actuator for horizontally positioning said at least one camera, and
   C. a third linear actuator for vertically positioning said at least one camera.

20. The method for inspecting and classifying a plurality of microscopic crystals as in claim 19, wherein said at least one camera is a first camera and a second camera, wherein said first camera is set at a constant zoom to cover a large field of view, wherein said second camera comprises a motorized zoom lens controllable by said at least one computer.

21. The method for inspecting and classifying a plurality of microscopic crystals as in claim 13, wherein said indexing device further comprises a bar-code reader and a micro-well plate sensing device.

22. The method for inspecting and classifying a plurality of microscopic crystals as in claim 13, wherein said at least one computer comprises a frame grabber for receiving images of said plurality of microscopic crystals from said at least one camera.

23. The method for inspecting and classifying a plurality of microscopic crystals as in claim 13, wherein said at least one computer is connected to a computer network.

24. The method for inspecting and classifying a plurality of microscopic crystals as in claim 23, wherein said at least one computer network is the Ethernet.

25. The method for inspecting and classifying a plurality of microscopic crystals as in claim 13, wherein said images of said plurality of microscopic crystals are color images.

26. The method for inspecting and classifying a plurality of microscopic crystals as in claim 25, wherein said color images are true color images wherein said step of taking the images of said plurality of microscopic crystals comprises the sub steps of:
   A) viewing each of said plurality of microscopic crystals through a first linear polarized filter and a second colored filter, wherein the color of said second colored filter is altered between red, green and blue, to obtain a first image, a second image and a third image, and
   B) combining said first image, said second image and said third image to obtain said true colored images.

27. The method for inspecting and classifying a plurality of microscopic crystals as in claim 25, wherein said color images are false color images wherein said step of taking the images of said plurality of microscopic crystals comprises the sub steps of viewing each of said plurality of microscopic crystals through a first linear polarized filter and a second linear polarized filter to obtain said false color images.

28. A device for inspecting and classifying a plurality of microscopic crystals, comprising:
   A) at least one camera means,
   B) an indexing means for sequentially placing said microscopic crystals in camera-view of said at least one camera means, and
   C) at least one computer means programmed to control said indexing means and said at least one camera means, wherein said at least one computer means is programmed to receive from said at least one camera means images of said plurality of microscopic crystals, wherein said at least one computer means is programmed to classify said plurality of microscopic crystals by:
1. comparing said images to a database stored on said at least one computer means, and
2. assigning a classification based on said comparison by:
   a. automatically making a first determination if said image is clear, and
   b. automatically making a second determination if said image is not clear, wherein said second determination is automatically chosen from a plurality of options, wherein said plurality of options comprises:
      i. at least one option corresponding to what is present if said microscopic crystal does not exist, and
      ii. at least one option corresponding to what is present if said microscopic crystal does exist.

29. The device for inspecting and classifying a plurality of microscopic crystals as in claim 28, further comprising a computer monitor means, wherein an operator interfacing with said at least one computer means manually inputs a score to classify said plurality of microscopic crystals after observing said plurality of microscopic crystals on said computer monitor means.

30. The device for inspecting and classifying a plurality of microscopic crystals as in claim 28, wherein said at least one computer means automatically classifies said plurality of microscopic crystals after receiving said images.

31. The device for inspecting and classifying a plurality of microscopic crystals as in claim 28, wherein said at least one camera means is a first camera and a second camera, wherein said first camera is set at a constant zoom to cover a large field of view, wherein said second camera comprises a motorized zoom lens controllable by said at least one computer means.

32. The device for inspecting and classifying a plurality of microscopic crystals as in claim 28, wherein each of said plurality of microscopic crystals are contained within a drop of liquid, wherein each drop of liquid is contained within a well of a micro-well plate.

33. The device for inspecting and classifying a plurality of microscopic crystals as in claim 28, wherein said plurality of microscopic crystals are a plurality of protein crystals inside the wells of at least one micro-well plate.

34. The device for inspecting and classifying a plurality of microscopic crystals as in claim 28, wherein said indexing means comprises:
A. a first linear actuator means for horizontally positioning said positioning station,
B. a second linear actuator means for horizontally positioning said at least one camera means, and
C. a third linear actuator mean is for vertically positioning said at least one camera means.

35. The device for inspecting and classifying a plurality of microscopic crystals as in claim 34, wherein said at least one camera means is a first camera and a second camera, wherein said first camera is set at a constant zoom to cover a large field of view, wherein said second camera comprises a motorized zoom lens controllable by said at least one computer means.

36. The device for inspecting and classifying a plurality of microscopic crystals as in claim 28, further comprising a bar-code reader means and a micro-well plate sensing means.

37. The device for inspecting and classifying a plurality of microscopic crystals as in claim 28, wherein said at least one computer means comprises a frame grabber means for receiving images of said plurality of microscopic crystals from said at least one camera means.

38. The device for inspecting and classifying a plurality of microscopic crystals as in claim 28, wherein said at least one computer means is connected to a computer network means.

39. The device for inspecting and classifying a plurality of microscopic crystals as in claim 38, wherein said at least one computer network means is the Ethernet.

40. A method for inspecting and classifying a plurality of microscopic crystals, comprising the steps of:
A) sequentially placing said plurality of microscopic crystals in camera-view of at least one camera utilizing an indexing device,
B) taking the images of said plurality of microscopic crystals with said at least one camera,
C) transferring said images to at least one computer,
D) receiving said images at said at least one computer, and
E) automatically classifying said images at said at least one computer, said step of automatically classifying said images at said at least one computer comprising the sub steps of:
   1) comparing said images to a database stored on said at least one computer, and
   2) assigning a classification based on said comparison, said step of assigning a classification based on said comparison comprising the sub steps of:
      a) automatically making a first determination if said image is clear, and
      b) automatically making a second determination if said image is not clear, wherein said second determination is automatically chosen from a plurality of options, wherein said plurality of options comprises:
         1. at least one option corresponding to what is present if said microscopic crystal does not exist, and
         2. at least one option corresponding to what is present if said microscopic crystal does exist,
wherein said at least one computer is programmed to control said at least one indexing device and said at least one camera.

41. A device for inspecting and classifying a plurality of microscopic crystals, comprising:
A) at least one camera,
B) an indexing device for sequentially placing said microscopic crystals in camera-view of said at least one camera, and
C) at least one computer programmed to control said indexing device and said at least one camera, wherein said at least one computer is programmed to receive from said at least one camera images of said plurality of microscopic crystals, wherein said at least one computer is programmed to automatically classify said plurality of microscopic crystals by:
   1) comparing said images to a database stored on said at least one computer, and 2) assigning a classification based on said comparison, said assigning a classification is accomplished by:

a) automatically making a first determination if said image is clear, and b) automatically making a second determination if said image is not clear, wherein said second determination is automatically chosen from a plurality of options, wherein said plurality of options comprises:

i. at least one option corresponding to what is present if said microscopic crystal does not exist, and ii. at least one option corresponding to what is present if said microscopic crystal does exist.

* * * * *